(12) United States Patent
McKean et al.

(10) Patent No.: US 12,194,159 B2
(45) Date of Patent: Jan. 14, 2025

(54) MULTILAYER POROUS MEMBRANE

(71) Applicant: THE ELECTROSPINNING COMPANY LTD, Didcot (GB)

(72) Inventors: Robert James McKean, Didcot (GB); Teodor-Matei Cirstea, Didcot (GB); Brendan Robb, Didcot (GB)

(73) Assignee: The Electrospinning Company Ltd, Didcot (GB)

( * ) Notice: Subject to any disclaimer, the term of this patent is extended or adjusted under 35 U.S.C. 154(b) by 848 days.

(21) Appl. No.: 17/280,616

(22) PCT Filed: Oct. 1, 2019

(86) PCT No.: PCT/GB2019/052767
§ 371 (c)(1),
(2) Date: Mar. 26, 2021

(87) PCT Pub. No.: WO2020/070484
PCT Pub. Date: Apr. 9, 2020

(65) Prior Publication Data
US 2022/0071920 A1 Mar. 10, 2022

(30) Foreign Application Priority Data
Oct. 1, 2018 (GB) .................................. 1816044

(51) Int. Cl.
A61K 9/70 (2006.01)
A61K 35/17 (2015.01)
(Continued)

(52) U.S. Cl.
CPC ................ A61K 9/70 (2013.01); A61K 35/17 (2013.01); A61K 35/18 (2013.01); B32B 5/022 (2013.01);
(Continued)

(58) Field of Classification Search
None
See application file for complete search history.

(56) References Cited

U.S. PATENT DOCUMENTS

2002/0173213 A1   11/2002   Chu et al.
2010/0150984 A1   6/2010    Kennedy et al.
(Continued)

FOREIGN PATENT DOCUMENTS

CN   101708344 A   5/2010
CN   101785875 A   7/2010
(Continued)

OTHER PUBLICATIONS

Sörenby, et al., "Preimplantation of an Immunoprotective Device Can Lower the Curative Dose of Islets to That of Free Islet Transplantation-Studies in a Rodent Model", Transplantation, vol. 86, No. 2, Jul. 27, 2008, 364-366.
(Continued)

Primary Examiner — Melissa S Mercier
(74) Attorney, Agent, or Firm — Vos-IP, LLC

(57) ABSTRACT

The invention relates to a therapeutic composition comprising an inner portion and a biocompatible membrane fully or partially surrounding the inner portion. The biocompatible membrane comprises at least two layers: a first layer of a porous, nonwoven network of thermoplastic polyurethane polymer fibers formed by electrospinning and having a porosity of greater than or equal to 50%; an average pore diameter of less than 5 μm; and has a thickness in the range 10 to 250 μm; and a second layer of a porous, nonwoven network of thermoplastic polymer fibers formed by electrospinning. The second layer has a mean average fiber diameter of the second layer is greater than the mean average fiber diameter in the first layer, and/or wherein the average pore diameter of the second layer is greater than the average pore diameter of the first layer. The inner portion comprises
(Continued)

a therapeutic agent. The invention also relates to uses of the membrane and therapeutic composition, for instance, to encapsulate therapeutic cells.

23 Claims, 11 Drawing Sheets

(51) Int. Cl.
A61K 35/18 (2015.01)
B32B 5/02 (2006.01)
B32B 5/26 (2006.01)
D04H 1/4358 (2012.01)
D04H 1/728 (2012.01)

(52) U.S. Cl.
CPC ........... *B32B 5/267* (2021.05); *D04H 1/4358* (2013.01); *D04H 1/728* (2013.01); *B32B 2262/0292* (2013.01); *B32B 2307/732* (2013.01); *B32B 2535/00* (2013.01)

(56) References Cited

U.S. PATENT DOCUMENTS

| 2012/0115386 A1 | 5/2012 | Jeong et al. |
| 2017/0325933 A1 | 11/2017 | Liu |
| 2018/0125632 A1 | 5/2018 | Cully et al. |

FOREIGN PATENT DOCUMENTS

| CN | 103623410 A | 3/2014 | |
| CN | 105497969 A | 4/2016 | |
| CN | 107596448 A | 1/2018 | |
| CN | 105169453 B | 3/2018 | |
| CN | 108498857 A | 9/2018 | |
| GB | 2518800 A | 4/2015 | |
| JP | H08-33472 A | 2/1996 | |
| JP | 2008-514341 A | 5/2008 | |
| JP | 2012-519559 A | 8/2012 | |
| JP | 2015-006400 A | 1/2015 | |
| KR | 10-2008-0105454 A | 12/2008 | |
| KR | 10-2017-0120823 A | 11/2017 | |
| WO | WO-2006080009 A2 * | 8/2006 | ............. A61F 2/022 |
| WO | WO/2008/039530 A2 | 4/2008 | |
| WO | WO/2008/112190 A1 | 9/2008 | |
| WO | WO/2013/117926 A1 | 8/2013 | |
| WO | WO-2015086550 A1 * | 6/2015 | ............. A61K 35/39 |
| WO | WO/2018/232180 A1 | 12/2018 | |
| WO | WO/2019/166764 A1 | 9/2019 | |

OTHER PUBLICATIONS

Wang, et al., "Tailored Fibro-Porous Structure of Electrospun Polyurethane Membranes, Their Size-Dependent Properties and Trans-Membrane Glucose Diffusion", Journal of Membrane Science, vol. 427, Oct. 7, 2012, 207-217.
International Search Report issued in International Application No. PCT/GB2019/052767 dated Dec. 11, 2019.
International Preliminary Report on Patentability issued in International Application No. PCT/GB2019/052767 dated Mar. 12, 2021.
Written Opinion of the International Preliminary Examining Authority issued in International Application No. PCT/GB2019/052767 dated Sep. 14, 2020.
Search Report issued in British Application No. GB1816044.0 dated Sep. 16, 2019.
Examination Report issued in British Application No. GB1914184.5 dated Jan. 21, 2022.
Search & Examination Report issued in British Application No. GB1816044.0 dated Jun. 28, 2019.
Search & Examination Report issued in British Application No. GB1914184.5 dated May 6, 2020.
Greiner, et al., "Electrospinning: A Fascinating Method for the Preparation of Ultrathin Fibers", Angewandte Chemie International Edition, vol. 46, No. 30, Jul. 13, 2007, 5670-5703.
Huang, et al., "A Review on Polymer Nanofibers by Electrospinning and Their Applications in Nanocomposites", Composites Science and Technology, vol. 63, No. 15, Jul. 2, 2003, 2223-2253.
Krishnan, et al., "Vascularization and Cellular Isolation Potential of a Novel Electrospun Cell Delivery Vehicle", Journal of Biomedical Materials Research Part A, vol. 102, No. 7, Jul. 31, 2013, 2208-2219.
Martinez, "An Efficient Algorithm to Calculate the Center of the Biggest Inscribed Circle in an Irregular Polygon", arXiv, vol. 1212.3193, Dec. 13, 2012.
Musiari, et al., "Feasibility Study of Adhesive Bonding Reinforcement by Electrospun Nanofibers", Procedia Structural Integrity, vol. 2, Jul. 21, 2016, 112-119.
Rianjanu, et al., "Solvent Vapor Treatment Improves Mechanical Strength of Electrospun Polyvinyl Alcohol Nanofibers", Heliyon, vol. 4, No. 4, Apr. 2, 2018, 1-19.
Schweicher, et al., "Membranes to Achieve Immunoprotection of Transplanted Islets", Frontiers in Bioscience—Landmark, vol. 19, No. 1, Jan. 1, 2014, 49-76.
Thanos, et al., "Considerations for Successful Encapsulated β-Cell Therapy", Cell Therapy: Current Status and Future (Humana Press), Aug. 25, 2017, 19-52.
Wang, et al., "Overcoming Foreign-Body Reaction Through Nanotopography: Biocompatibility and Immunoisolation Properties of a Nanofibrous Membrane", Biomaterials, vol. 102, Jun. 15, 2016, 249-258.
Weber, et al., "Automated Control of the Laser Welding Process of Heart Valve Scaffolds", Current Directions in Biomedical Engineering, vol. 2, No. 1, Sep. 30, 2016, 301-305.
Wirth, et al., "Preliminary Study of Ultrasonic Welding as a Joining Process for Electrospun Nanofiber Mats", Nanomaterials, vol. 8, No. 10, Sep. 20, 2018, 1-13.
You, et al., "Thermal Interfiber Bonding of Electrospun Poly(L-Lactic Acid) Nanofibers", Materials Letters, vol. 60, No. 11, Dec. 9, 2005, 1331-1333.
Zhou, et al., "The Thermal Conductivity of Nylon 6/clay Nanocomposites", Journal of Applied Polymer Science, vol. 108, No. 6, Mar. 25, 2008, 3822-3827.
Zondervan, et al., "Design of a Polyurethane Membrane for the Encapsulation of Islets of Langerhans", Biomaterials, vol. 13, No. 3, 1992, 136-144.
Zhuo, et al., "Preparation of Polyurethane Nanofibers by Electrospinning", Journal of Applied Polymer Science, vol. 109, No. 1, Mar. 28, 2008, 406-411.
Search & Examination Report issued in Israeli Application No. IL281735 dated Oct. 27, 2022.
Lu, et al., "Tumor-Penetrating Microparticles for Intraperitoneal Therapy of Ovarian Cancer", Journal of Pharmacology and Experimental Therapeutics, vol. 327, No. 3, Sep. 9, 2008, 673-682.

* cited by examiner

MULTILAYER POROUS MEMBRANE

CROSS-REFERENCE TO RELATED APPLICATIONS

This application is a 371 National Phase Entry of International Patent Application No. PCT/GB2019/052767 filed on Oct. 1, 2019, which claims the benefit of British Patent Application No. 1816044.0 filed on Oct. 1, 2018, the contents of which are incorporated herein by reference in their entirety.

FIELD OF THE INVENTION

The invention relates to a biocompatible membrane which allows the selective passage of materials to target cells in vivo. In particular the invention relates to a therapeutic composition comprising an inner portion and a biocompatible membrane fully or partially surrounding the inner portion; wherein the biocompatible membrane comprises a porous, nonwoven network of thermoplastic polyurethane polymer fibers formed by electrospinning. The invention also relates to a process for producing the membrane and to uses of the membrane in therapy.

BACKGROUND OF THE INVENTION

Diabetes mellitus is a condition in which the body does not produce enough, or does not respond to, insulin. According to the Center for Disease Control and Prevention, more than 29 million people in the United States are living with diabetes mellitus, and 86 million are living with prediabetes, a serious health condition that increases a person's risk of type 2 diabetes and other chronic diseases. Of the total population with diabetes, approximately 5%, or almost 1.5 million in the US, have type 1 diabetes (T1D). In 2010, it was estimated that the annual cost of T1D to the US healthcare system was approximately $14.4 billion. Type 1 diabetes is an autoimmune disease in which the patient's immune system goes awry and attacks and destroys the pancreatic beta (ß) cells. Beta cells are responsible for regulating blood sugar (glucose) levels by producing precise amounts of the essential hormone insulin. Patients with T1D, and many with type 2, require insulin to survive. As beta cell loss is the primary pathogenesis of T1D, the disease is an ideal candidate for cell replacement therapy.

Cell therapy has been proposed for the treatment of diabetes. Cells must respond to blood/serum glucose level by releasing, or not releasing, insulin. There are a number of companies developing cell therapies, either pancreatic ß cells or stem cells that will differentiate to ß cells. To be successful in vivo the cells need to be implanted in a membrane pouch (or equivalent) with the following desirable characteristics:

Facilitate (or at least permit) vascularization;
Allow flux of glucose and insulin molecules;
Prevent host immune cells from getting in and destroying introduced cells;
Prevent introduced cells escaping into host (where they could cause cancer);
Support vital cells for 2 years (current commercial target);
Allow easy removal (in case something goes wrong).

To date, a material meeting all of these characteristics has not yet been found.

There remains a need to provide improved materials for the encapsulation of cellular materials within the body.

SUMMARY OF THE INVENTION

The desirable characteristics discussed above are provided by the present invention, particularly by a therapeutic composition comprising a membrane as set out in claim 1.

The present invention makes use of a biocompatible membrane which can act as a size selective membrane or a "molecular sieve," for controlling the delivery of external substances to particular target cells both in vitro and in vivo. The membrane comprises pores of a suitable size such as to allow the passage of solute molecules such as glucose, but to prevent the passage of larger particles such as cells. The membrane can be packaged together with the target cells of interest, optionally on a scaffold, to provide artificial tissues and organs for use in the treatment of disease. Advantageously, the membrane can shield any encapsulated cells from the host's immune system.

The membrane of the invention is shaped to form a therapeutic composition which takes the form of a "pouch" or "bag" which contains a therapeutic agent. The therapeutic agent is encapsulated by the membrane. As mentioned above, the membrane is selectively permeable such that certain molecules can pass through. When the therapeutic agent is cells, these are generally held in place permanently inside the membrane interior (pouch). However, when the therapeutic agent is a smaller entity, such as a drug molecule, this may diffuse out of the pouch through the membrane and enter the patient.

Accordingly, in a first aspect, the present invention provides a therapeutic composition (5,6) comprising an inner portion (7) and a biocompatible membrane (4, 10) fully or partially surrounding the inner portion; wherein the biocompatible membrane comprises at least two layers: a first layer (1) of a porous, nonwoven network of thermoplastic polyurethane polymer fibers formed by electrospinning and having a porosity of greater than or equal to 50%; an average pore diameter of less than 5 µm; and has a thickness in the range 10 to 250 µm; and a second layer (2) of a porous, nonwoven network of thermoplastic polymer fibers formed by electrospinning, wherein the mean average fiber diameter of the second layer (2) is greater than the mean average fiber diameter in the first layer (1); and/or wherein the average pore diameter of the second layer (2) is greater than the average pore diameter of the first layer (1); and wherein the inner portion (7) comprises a therapeutic agent (3).

In some embodiments, the second layer (2) is defined as having a porosity which is substantially equal to or higher than the porosity of first layer (1).

In some embodiments, the second layer (2) is defined as having a mean average fiber diameter greater than the mean average fiber diameter in the first layer (1).

In some embodiments, the second layer (2) is defined as having the average pore diameter greater than the average pore diameter of the first layer (1).

In some embodiments, the second layer (2) is defined as having a porosity which is substantially equal to or higher than the porosity of first layer (1) and the mean average fiber diameter of the second layer (2) is greater than the mean average fiber diameter in the first layer (1). In some embodiments, the second layer (2) is defined as having a porosity which is substantially equal to or higher than the porosity of first layer (1) and wherein the average pore diameter of the second layer (2) is greater than the average pore diameter of the first layer (1). In some embodiments, the second layer (2) is defined as having a mean average fiber diameter greater than the mean average fiber diameter in the first layer (1) and wherein the average pore diameter of the second layer (2) is greater than the average pore diameter of the first layer (1).

In some embodiments, the fibers of the second layer (2) may be polyurethane, whilst in other they may be as defined herein or may be any other biocompatible, thermoplastic polymer or polymer blend. In some embodiments, the biocompatible membrane (4, 10) is in the form a pouch or bag (5, 6, 11) which partially or fully encapsulates the inner portion (7) comprising the therapeutic agent (3). In some embodiments, the therapeutic composition further comprises a carrier (8) on or in which the therapeutic agent (3) is disposed, preferably wherein the therapeutic agent (3) is: attached to the surface of the carrier (8); disposed in pores of the carrier (8); and/or encapsulated within the carrier (8).

In some embodiments, the pouch or bag (6) is arranged such that the first layer (1) faces or is in contact with the encapsulated inner portion (7) and, optionally, the therapeutic agent (3); whilst the second layer (2) faces externally. In some embodiments, the pouch or bag (5) is arranged such that the first layer (1) faces externally; whilst the second layer (2) faces or is in contact with the encapsulated inner portion (7) and, optionally, the therapeutic agent (3). In some embodiments, the pouch or bag (5) is arranged such that the first layer (1) faces externally; whilst the second layer (2) faces or is in contact with the encapsulated inner portion (7), the carrier (8) and, optionally, the therapeutic agent (3). In some embodiments, the biocompatible membrane (10) comprises three layers: a first layer (1) provided between two second layers (2), wherein the inner portion (7) is provided within an internal-facing surface of one of the second layers (2) when the biocompatible membrane (4) is in the form the pouch or bag (11); with the other of the two second layers (2) providing an external-facing surface; and wherein a carrier is optionally disposed within the inner portion (7).

In some embodiments, the first layer (1) has a porosity in the range 50% to 90%, optionally 50% to 80%. In some embodiments, the first layer (1) has an average pore diameter of less than 2 µm. In some embodiments, the first layer (1) has a thickness in the range 10 to 150 µm, preferably in the range 20 to 150 µm, most preferably in the range 50 to 150 µm or 50 to 200 µm. In some embodiments, the mean diameter of the polymer fibers of the first layer (1) is less than 700 nm, preferably less than 600 nm, preferably less than 500 nm and is most preferably in the range 100-500 nm, even more preferably in the range 50-500 nm.

In some embodiments, the second layer (2) is or comprises polyurethane or any other biocompatible, thermoplastic polymer or polymer blend and/or other thermoplastic polymer, optionally those described herein, including polyethylene.

In some embodiments, the first layer (1) and/or the second layer (2) of the biocompatible membrane (4, 10) are non-biodegradable. In some embodiments, the therapeutic agent (3) is selected from therapeutic cells, a drug, a nucleic acid, a polynucleotide, a protein, a polypeptide, an antibody, a particle such as lipid nanoparticle, an extracellular vesicle or exosome, optionally wherein the polynucleotide comprises DNA, RNA, RNAi, saRNA or siRNA. In some embodiments, the biocompatible membrane (4) fully or partially surrounds the carrier. In some embodiments, the carrier (8) comprises a porous, nonwoven network of polymer fibers or a hydrogel, gelatin, collagen (optionally fibers or sponges) or decellularized tissue. In some embodiments, the composition comprises cells (3), wherein the cells are preferably pancreatic R cells or islet cells.

In some embodiments with an externally-facing second layer, the second layer (2) further comprises a hydrogel, gelatin, or collagen (optionally fibers or sponges), or decellularized tissue.

In some embodiments, the second layer (2) is formed from electrospun fibers, and (i) the porosity is in the range 70% to 98%, preferably in the range 80 to 95%; and/or (ii) the average pore diameter is in the range 5 to 80 µm, preferably in the range 10 to 50 µm; and/or (iii) the mean diameter of the polymer fibers is in the range 1 to 10 µm, preferably in the range 2 to 8 µm, most preferably in the range 3 to 7 µm.

In some embodiments: (i) the porosity of the second layer (2) is within at least 120%, 110%, 100% of the porosity of the first layer (1), optionally 100% to 110%, 100% to 150%, 100% to 175%, or 100% to 190%, or 100% up to 199% or 200% compared to the porosity of the first layer (1); and/or (ii) the average pore size/diameter of the second layer (2) is at least 2 times, at least 5 times, at least 10 times, at least 20 times, at least 50 times or at least 100 times the pore size/diameter of the first layer (1); and/or (iii) the mean diameter of the polymer fibers of the second layer (2) is at least 2 times, at least 5 times, at least 10 times, at least 20 times, at least 50 times or at least 100 times the diameter of the first layer (1).

Any combination of the above is envisaged. In some embodiments the term 'the second layer (2) having a porosity which is substantially equal to or higher than the porosity of first layer (1) means that the second layer has a great porosity than the first layer. In some embodiments, this term means that the porosity is substantially equal to than the porosity of first layer, which may mean that the porosity of the second layer is exactly equal, for example to 2 significant figures, to the porosity of first layer. It is also envisaged, in some embodiments that the porosity of the second layer may be slightly less than the porosity of first layer and, for example, a 5% variance here is envisaged.

In some embodiments, the therapeutic composition further comprises one or more additives, wherein the additives are preferable disposed within the carrier (8) or one or both of the first layer (1) or the second layer (2), further wherein the additives are selected from growth factors such as vascular endothelial growth factor (VEGF), crosslinking agents, Growth factors, Catalase and other enzymes; or an oxygen-releasing material such as $CaO_2$ or Hemoglobin, Peroxides (for instance, $H_2O_2$, $CaO_2$, $MgO_2$, $Li_2O_2$, $Na_2O_2$), Sodium Percarbonate ($Na_2CO_3$), Perfluorocarbons, Hydroxyapatite, Tricalcium phosphate (bone growth promoting materials), most preferably $CaO_2$ and/or $MgO_2$.

In some embodiments, the porosity of the second layer (2) is within at least 120%, 110%, 100%, 90%, or 80% of the porosity of the first layer (1).

In some embodiments, the average pore size/diameter of the second layer (2) is at least 2 times, at least 5 times, at least 10 times, at least 20 times, at least 50 times or at least 100 times the pore size/diameter of the first layer (1). In some embodiments, the pore size/diameter of the second layer (2) is up to 100 times the pore size/diameter of the first layer (1). In some embodiments, the pore size/diameter of the second layer (2) are 2 to 5, 2 to 10, 2 to 20, 2 to 50, 2 to 100, 5 to 10, 5 to 20, 5 to 50, 5 to 100, 10 to 20, 10 to 50, 10 to 100, 20 to 50, 20 to 100, or 50 to 100 times the pore size/diameter of the first layer (1).

In some embodiments, the polymer fibers of the second layer (2) have a larger diameter than the polymer fibers of the first layer (1). In some embodiments, the mean diameter of the polymer fibers of the second layer (2) is at least 2 times, at least 5 times, at least 10 times, at least 20 times, at least 50 times or at least 100 times the diameter of the first layer (1). In some embodiments, the polymer fibers of the second layer (2) are up to 100 times the diameter of the first layer (1). In some embodiments, the polymer fibers of the second layer (2) are 2 to 5, 2 to 10, 2 to 20, 2 to 50, 2 to 100, 5 to 10, 5 to 20, 5 to 50, 5 to 100, 10 to 20, 10 to 50, 10 to 100, 20 to 50, 20 to 100, or 50 to 100 times the diameter of the first layer (1).

An advantage of the arrangement wherein the or one of the second layers (2) has an internal-facing surface (for example as shown in shown in FIGS. 10 and 13) is that no carrier is necessarily required. Instead, the second layers (2) serve to function as a carrier.

In a second aspect, there is also provided a membrane comprising at least two layers, wherein (i) the first layer (1) is a biocompatible membrane comprising a porous, nonwoven network of thermoplastic polyurethane polymer fibers formed by electrospinning, wherein the biocompatible membrane has a porosity of greater than or equal to 50%; an average pore diameter of less than 5 μm; and has a thickness in the range 10 to 250 μm; and (ii) the second layer (2) is disposed on the first layer and wherein the second layer (2) is of a porous, nonwoven network of thermoplastic polymer fibers formed by electrospinning, which fibers of the second layer (2) may or may not be polyurethane, the second layer (2) having an the mean average fiber diameter of the second layer (2) is greater than the mean average fiber diameter in the first layer (1), and/or wherein the average pore diameter of the second layer (2) is greater than the average pore diameter of the first layer (1).

In some embodiments, the first layer (1) and/or the second layer (2) is as defined herein.

In any one of the aspects, a membrane or a therapeutic composition may be, in some embodiments, for use in a method for treatment of the human or animal body by therapy. In some embodiments, the membrane or a therapeutic composition may be for use in a method of treating (preferably type 1) diabetes.

Provided is a method of treatment of the human or animal body in need thereof comprising administering to the human or animal body a therapeutically effective amount of a therapeutic composition, or for use in a method of immunoprotecting therapeutic cells or in a method of treating (preferably type 1) diabetes. Also provided is a device comprising the therapeutic composition, wherein the inner portion comprises pancreatic beta or islet cells, with or without the carrier material. Also provided is device comprising the therapeutic composition, wherein the inner portion comprises hepatocytes. Also provided is a device comprising the therapeutic composition, wherein the inner portion comprises erythrocytes and/or leukocytes (for example B-cells or T-cells), preferably engineered leukocytes such as engineered T-cells, including CAR-T-cells (Chimeric Antigen Receptor T-cells).

In a third aspect, there is provided a process for producing a therapeutic composition, comprising (i) an electrospinning process to produce a biocompatible membrane (4) comprising a porous, nonwoven network of thermoplastic polyurethane polymer fibers; and (ii) shaping the biocompatible membrane to produce a therapeutic composition in which an inner portion (7) is fully or partially surrounded; the shaping being optionally by welding edges.

Advantageously the membrane of this invention, according to any of its aspects, is permeable to many biomolecules (typically of less than 100 nm in size, for instance glucose), but blocks the passage of molecules/particles greater than this size. Advantageously the membrane is impermeable to the passage of cells.

The membrane used in the invention can be used to encapsulate target cells of interest and thus control the microenvironment of the cells. The porous nature of the network of polymer fibers allows solutes to pass through the membrane and thus reach target cells of interest. Thus the cells are sustained, and viability is maintained. However, the pore size is controlled such that larger molecules, such as cells, cannot pass through the membrane. Thus introduced cells are prevented from escaping from a host (which is vital from a regulatory perspective). Furthermore, host immune cells are prevented from accessing the target cells and destroying them. Finally, the membrane allows the target cells to be isolated and removed from the host should this prove necessary.

Thus, the invention meets many of the desirable characteristics outlined above.

Figure 10:
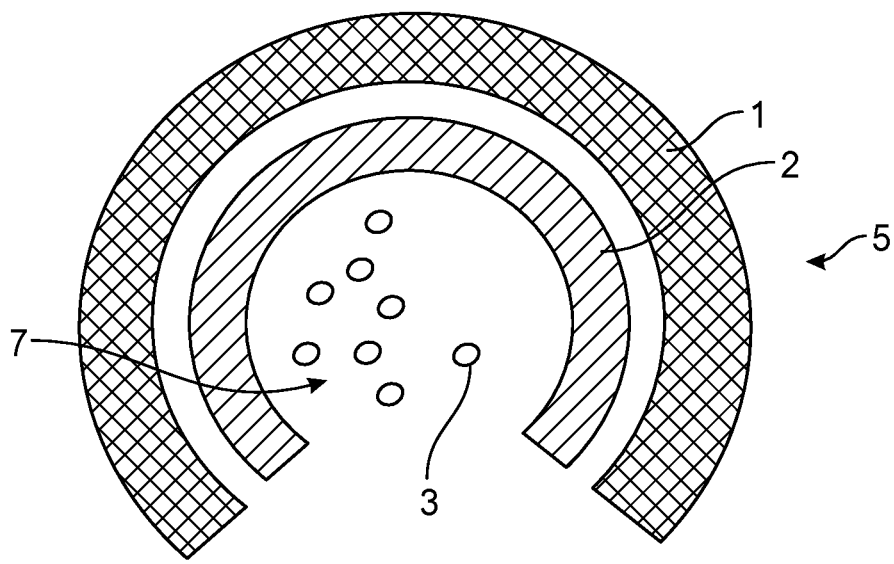
FIG. 10 shows biocompatible membrane (4) from FIG. 9 being folded (in 2D, but equally this applies in 3D) to form one arrangement whereby the layer (1) with the smaller diameter fibers faces externally, so as to be contactable with the subcutaneous environment of the patient into which the bag or pouch (5) is to be provided. The layer (2) with the larger diameter fibers faces internally, so as to be contactable with the therapeutic agent (in this case cells [3] supported on a carrier [8]) that may be placed within the inner portion (7) of the bag or pouch (5).

An advantage of the arrangement shown in FIGS. 10 and 13 (i.e. wherein the or one of the second layers (2) has an internal-facing surface) is that no carrier is necessarily required. Instead, the second layers (2) serve to function as a carrier.

DETAILED DESCRIPTION OF THE INVENTION

Schweicher, et al; *Front Biosci* (Landmark Ed). 2014; 19: 49-76, "Membranes to achieve immunoprotection of transplanted islets" provides a review of the use of semipermeable membranes to encapsulate and immunoprotect transplanted islet or beta cells for the treatment of diabetes. The article outlines that despite many promising encapsulation studies and the development of numerous devices, cell encapsulation has yet to make an impact in the clinical setting. Some of the factors limiting widespread application of encapsulated islets include incomplete isolation of islets from the immune system and inadequate physiological nutrient accessibility for cells within the devices.

Devices for the encapsulation of cells have made use of various organic and inorganic materials. Amongst the organic (polymeric) materials, hydrogels have to date found the most success, although thermoplastic polymers have also been used due to their mechanical and chemical stability. The use of polyurethane is mentioned in Zondervan, et al; "Design of a polyurethane membrane for the encapsulation of islets of Langerhans." *Biomaterials.* 1992; 13(3):136-144. However, the use of electrospinning to produce the polyurethane is not disclosed.

Zhuo, et al; *J Appl Polym Sci,* 2008 disclose a method of preparation of polyurethane nanofibers by electrospinning. The resultant nanofibers, electrospun from DMF solutions, had ultrafine diameters ranging from about 700 to 50 nm. In particular, it was found that the solution concentration played a main role in influencing the transformation of the polymer solution into ultrafine fibers, and the diameters increased with the solution concentrations increasing.

WO/2008/112190 provides a bioartificial pancreas and a method to produce it in order to produce insulin in diabetic animals. The bioartificial pancreas contains a perforated midsection with a filling port used to introduce insulin-producing cells, upon which a biologically compatible polymer network is deposited along with the formation of an immunoisolatory membrane on the midsection.

WO/2008/039530 provides a tissue engineered intervertebral disc comprising an inner layer and an exterior layer, wherein the exterior layer is a nanofibrous polymer support comprising polymer nanofibers and the inner layer comprises a hydrogel composition into which therapeutic cells are placed and cultured.

US 2017-0325933 A1 provides an artificial blood vessel comprising a fibroblast layer, smooth muscle layer, endothelial cell layer and an inner cavity all surrounded by a cortex layer of synthetic polymer produced by methods including electrospinning.

CN107596448 provides a biological membrane stent material and a process for producing said membrane, where the membrane comprises outer, middle, and inner layers. The inner layer comprises an electrospun fiber membrane constituted from polyurethane, the middle layer comprises a mixture of polyurethane and polycaprolactone with Ca salts and the outer layer comprises polycaprolactone with Ca salts.

CN103623410 provides an antibacterial composition and an implant using said antibacterial composition in the production of artificial organs and tissues for use in the body. The antibacterial composition is coated with polyurethane through high-pressure electrospinning to form an antibacterial agent contained within the boundaries of the thermoplastic polyurethane elastomer.

CN101785875 provides the preparation method of a superfine nanofibrous vascular prosthesis which uses polyurethane electrospinning to produce a prosthesis with high porosity, facilitating material exchange while inhibiting the proliferation of cells to subendothelial layers of the adjacent blood vessel.

CN101708344 provides a nanofiber vascular prosthesis and a method for its production. The inner portions of the vascular prosthesis are prepared by mixing solutions of gelatin and glacial acetic acid with crosslinkers and heparin sodium, after which polyurethane is added as an outer layer by electrospinning. The inner layer improves blood compatibility, and the outer layer has biological stability and can improve physical and mechanical properties.

CN108498857 provides a preparation method for artificial fullerene-carried nucleus pulposus, comprising an inner layer of xerogel around which is coated a polyurethane membrane by electrospinning. This contains the xerogel without influencing its hydration and size properties and prevents unwanted movement of the xerogel implant and enhances the storage life of such devices.

GB2518800 provides a duodenum endothelium membrane obtained from an electrospun biocompatible material which can be used to treat diabetes mellitus and adiposis. The duodenum endothelium membrane is placed into the duodenum to inhibit the contact of food with the intestinal mucosae and to prevent its physiological impact on the cells of the intestinal mucosae. The material is obtained from electrospinning, providing beneficial medical device properties, including greater adhesion, reduced injury, and greater bounce restraint.

WO/2006/080009 A2 provides an implantable bioreactor, wherein a first compartment is in capable of maintaining fluid communication with the vasculature of a patient, and a second compartment is configured for containing cells, with the compartments separated by a membrane. The membrane separating the compartments, or the device as a whole, can be fabricated from electrospun materials, including electrospun polyurethane. The device can be used in the treatment of diabetes, for which the cells in the cell compartment are insulin-secreting cells.

Luo, et al. (*Biomaterials* (102 (2016) 249-258) describes the use of two identical electrospun polyurethane membranes sandwiched between two PET Meshes. The aim is to produce implantable immunoisolation membranes, containing therapeutic cells, and to prohibit fibrotic deposition after implantation, which can impact the supply of nutrients to the cells within. It provides a flat microencapsulation device based on the biocompatible membranes. The separate PET mesh is used to provide structural stability.

Referring now to the present invention, the inner portion comprises the interior of the therapeutic composition. It is fully or partially surrounded by the biocompatible membrane. By "surrounding" we mean that the biocompatible membrane envelopes or encloses the inner portion in three dimensions, meaning the inner portion is typically at least 50%, more preferably 60%, 70%, 80%, 90% or 95% surrounded by the biocompatible membrane.

The inner portion is generally not hollow but is formed from a substantially continuous mass. The inner portion may, for instance, comprise a carrier (including a scaffold), onto or into which the therapeutic agent is disposed. Accordingly, the therapeutic composition is generally a fully enclosed continuous mass with an inner portion encapsulated by the biocompatible membrane.

The therapeutic composition is generally not tubular in shape—i.e. preferably it does not have a hollowed out portion in contact with the exterior environment. The therapeutic composition may take the form of a package, pouch, or bag.

In the context of the invention, the terms "pouch" and "bag" have their usual meanings, indicating a nonrigid container where the material constituting the pouch or bag forms the outer boundary of the environment in which the intended contents can be placed, precluding the ingress and egress of the intended contents from points other than the intended entrance and exit of the pouch or bag. The said entrance and exit can be sealed to wholly surround the innards of the pouch or bag with the material constituting the pouch or bag. In the present invention, the biocompatible membrane forming a pouch or bag is impermeable with respect to the therapeutic agent, and therefore functions as a bag or pouch in restraining the therapeutic agent, while being permeable to selected molecules smaller than the therapeutic agent. A pouch or bag of the present invention can adopt a variety of shapes and structures based on, inter alia, circles, squares, and other polygons to form, inter alia, discs, cuboids and other polyhedra.

The pouch or bag may be approximately spherical in shape. It may have an average largest diameter in the range 0.5-10 cm, preferably 1-5 cm.

In the context of the invention, the carrier is defined herein and may include a scaffold, as also referred to herein. For example, the carrier can be either a hydrogel or collagen fibers, but the collagen could also be described as scaffold.

In some embodiments, the therapeutic composition (5,6) is formed in the shape of a biconcave disc, for example similar to a red blood cell (erythrocyte). An example is shown in as (9) in FIG. 12. An O-ring of suitable material may, for example, be used to help form and maintain the biconcave disc shape by providing structure around the periphery of the biconcave disc.

By partially surrounded, we mean that the biocompatible membrane does not fully surround the inner portion but provides a degree of coverage. The inner portion is typically at least 50%, more preferably at least 60%, 70%, 80%, 90% or 95% surrounded by the biocompatible membrane.

By fully surrounded, we mean that the biocompatible membrane completely covers, envelopes or encloses the inner portion, such that the inner portion is completely encapsulated by the biocompatible membrane (i.e. 100% surrounded).

The membrane according to this invention is a sheet-like polyurethane material which is produced by electrospinning. Electrospinning polyurethane according to this invention provides a material which is structurally distinct to the polyurethane material produced by the methods disclosed in Zondervan, et al. discussed above, wherein the polyurethane network was formed by crosslinking a mixture of linoleic acid and a linear poly(etherurethane) with dicumyl peroxide. The electrospinning process results in a network of polyurethane fibers which is more uniform and tunable, compared to methods of the prior art.

Preferably, the fibers are nanofibers. The term "nanofiber" means a microscopic fiber whose diameter is conveniently measured in nm or μm.

Thus, the mean diameter of the polymer fibers in the membrane is less than 1000 nm, typically less than 900 nm, 800 nm, 700 nm, 600 nm or 500 nm, and is most preferably in the range 100-500 nm or 50-500 nm. The relative standard deviation of the fiber diameter distribution around the mean fiber diameter is typically less than or equal to 30%.

Typically, the mean diameter of the polymer fibers in the scaffold is measured by Scanning Electron Microscopy (SEM). Usually the standard deviation from the mean is also measured by SEM.

The network of fibers is a random distribution of fibers in space that forms an interconnecting net with spacing between the fibers. The network has small spaces between the fibers comprising the network, forming pores or channels in the network, which allow fluid to pass through.

The porous network of fibers is a nonwoven network, i.e. the fiber is typically randomly orientated in the porous network. Thus, the polymer fibers in the porous, nonwoven network of fibers do not have any particular orientation to speak of, i.e. the fiber in the porous, nonwoven network is typically randomly orientated or at least approaching random orientation. The degree of alignment of the polymer fibers in the membrane is therefore low, if not entirely random.

The membrane, which may be referred to as a barrier membrane, is size selective i.e. selectively porous to molecules or particles of a certain size. The following discussion regarding a barrier membrane particularly applies to the first layer (1).

Thus the membrane according to this invention acts as a size selective barrier. The porous membrane is not permeable to cells. The pores or channels in the membrane are large enough to allow diffusion of ions, metabolites, proteins, and/or bioactive molecules (e.g. glucose) but prevent cells from penetrating and permeating the nanofiber network. Flow of fluid and molecules through a membrane can be measured using techniques which are known in the art, and an example is described herein.

The flux properties of therapeutic molecules and nutrients may be in the range of $1\times10^{-6}$ cm$^2$/s to $1\times10^{-7}$ cm$^2$/s, ideally with values no lower than $1\times10^{-5}$ cm$^2$/s. Flux properties should be comparable to other types of barrier membranes described in the literature (Thanos, C. G., Gaglia, J. L. & Pagliuca, F. W. in Cell Therapy: Current Status and Future Directions 19-52 (Humana Press, Cham, 2017)).

The barrier membrane according to this invention may be defined as a thin, pliable, sheet-like layer of material which comprises the network of fibers. It may act as a boundary or lining. For instance, the membrane may act as a partition in a living organism.

A typical barrier membrane of the invention has a thickness in the range 25 to 250 μm, for instance, 10 or 20 to 150 μm.

The barrier membrane typically has a porosity which is equal to or greater than 50%, for instance greater than or equal to 60%, 65%, 70%, 75%, 80%, 85% or 90%. In other words, the membrane typically has greater than 50%, for instance greater than or equal to 60%, 65%, 70%, 75%, 80%, 85% or 90% air, by volume (when the membrane is not permeated with fluid). In a preferred embodiment the porosity is in the range 50-80%.

The porous network of polymer fibers in the barrier membrane may have a mean pore size of, for example, from 0.5 to 100 μm, for instance 1 μm to 10 μm, preferably less than 20, 15, 10 or 5 μm. An islet of Langerhans in the pancreas typically has a diameter of 100-200 μm, so such pores will prevent the passage of such cells. Pore size can be difficult to measure accurately, though, as pore size depends on how far through the scaffold one measures, and no two pores are the same shape due to the random orientation of the nanofibers. To address this, the pore size can be measured by taking an SEM and fitting the biggest inscribed circle inside the irregular polygon of the pore. The mean average can then be calculated for a given sample of the membrane.

The pore size is tuned to be less than a typical cell diameter (approximately less than 20 microns). Such porosity is beneficial in preventing cells from proliferating through the membrane of the scaffold. Pore size can be calculated from average pore area using the following equation:

$$2\sqrt{\frac{A}{\pi}} = d$$

Equation 1: Formula Used to Convert Average Pore Area A) into Average Pore Diameter (d).

Exemplary pore sizes may be defined in this invention as the diameter of the largest inscribed circle that can be fit into an irregular polygon as formed by the crossing of three or more fibers. A mathematical description of this process can be found in Martinez, O. "An Efficient Algorithm to Calculate the Center of the Biggest Inscribed Circle in an Irregular Polygon" (2012).

The membrane may have a gradient of pore size, porosity, or average fiber diameter. In one preferred embodiment of the invention, the membrane has a bilayer structure wherein the pore size, porosity and/or average fiber diameter is different in the two layers.

The porosity, average pore diameter and the average fiber diameter of a nonwoven network are interrelated, as explained for instance in Greiner and Weddorff, *Angew. Chem. Int. Ed.* 2007, 46, 5670-5703.

The polymer used to form the membrane is a biocompatible polymer. The membrane is non-cytotoxic. Preferably the polymer is not a bioerodible or biodegradable polymer. The polymer is a thermoplastic polyurethane polymer. Generally the polyurethane is a permanent (nonresorbable) polymer. This enables the therapeutic composition to be easily removed from the body, should this ever be necessary.

The thermoplastic polyurethane, may, in some embodiments be Polycarbonate-urethane. The thermoplastic polyurethane, may, in some embodiments be Silicone-Polycarbonate-urethane. The thermoplastic polyurethane, may, in some embodiments be Polyether-urethane. The thermoplastic polyurethane, may, in some embodiments be Silicone-polyether-urethane. The thermoplastic polyurethane, may, in some embodiments be Polyester-urethane. The thermoplastic polyurethane, may, in some embodiments be Polyol-urethane. The thermoplastic polyurethane, may, in some embodiments be Polyester-ether-urethane.

The membrane according to this invention may comprise other constituents, in addition to the network of polymer fibers.

The polymeric network which forms the membrane is generally homogenous, malleable into different forms, and has controllable architecture and properties.

Therapeutic compositions according to this invention comprise the membrane according to the first aspect of the invention together with a therapeutic agent, for instance, one or more drugs or cells. The membrane may partially or fully encapsulate the therapeutic agent. The membrane typically forms the outer portion of the therapeutic composition, and the therapeutic agent forms the inner portion.

Cells which are microencapsulated by the membrane of the present invention may be supported on or in a carrier, which is preferably a scaffold. The scaffold which supports the cells in this invention may advantageously further comprise a component that is suitable for providing mechanical strength and for maintaining the integrity of the open pore structure of the porous network of fibers. This second component can advantageously restrict deformation or stretching of the porous network of fibers, and thereby minimize consequential adverse changes to the porosity and pore size of the porous network that facilitates cell growth. Methods for preparing scaffolds with cells disposed thereon are disclosed in WO/2013/117926.

The scaffold is suitable for supporting cell growth and generally comprises a porous network of fibers. The fibers are typically polymeric. The scaffold of the invention may be elongate, or cylinder-shaped.

Alternatively, the therapeutic agent may be mixed with a different carrier material. Suitable materials include hydrogels, polymer foams and decellularized tissue, and/or alginate.

The barrier membrane, i.e. the first layer (1) may be surrounded, in some embodiments, by an outer layer of material, for example the second layer (2). The outer layer (second layer) may fully or partially surround the barrier membrane (first layer). Typically, this outer layer of material forms a further layer on top of the biocompatible membrane.

The outer layer may act to promote adhesion and vascularization in vivo. The outer layer may be formed from electrospun fibers and/or other carrier scaffold materials (for instance, hydrogel, gelatin foams, decellularized tissue etc.).

This outer layer is discussed further below, in the context of a cell encapsulation device.

Therapeutic compositions of the invention can be used to implant therapeutic cells into a target tissue, for instance into a damaged or diseased tissue, more effectively. For instance, such a therapeutic composition is capable of providing the cells with access to the optimal location in the body. The therapeutic composition of the invention may act as an organ substitute. The cells may be, for instance, pancreatic R cells, and the therapeutic composition may act as an artificial therapeutic pancreas. Alternatively the cells may be stem cells.

Thus the therapeutic composition may be useful for the treatment of diabetes, in particular the treatment of diabetes type 1.

In some embodiments, the cell type or treatment may be associated with any one or more of the following. In some embodiments, the therapeutic use or cell types are those associated with diabetes cell therapies: not only pancreatic R cells but also those cells on the developmental path toward them, for example iPSC, hPSC and/or hES, pancreatic progenitor, endocrine progenitor, and pcell.

In general, and in some embodiments, the cell types may be any stem cell or progenitor cell. Examples may be cells (including stem cells or progenitor cells) that will differentiate into a desired phenotype.

In some embodiments, the therapy is for AMD (Age-related Macular Degeneration). In some embodiments, the cell types may therefore be retinal pigment epithelial cells.

In some embodiments, the therapy is for hemophilia or cancer, especially blood cancers such as leukemia. In some embodiments, the cell types may therefore be hepatocytes producing factor IX (FIX) and factor XIII.

In some embodiments, the cells me be or include one or more genetically modified cells. For example leukocytes. In some embodiments, the leukocyte(s) may have been extracted from the patient or a tissue match and engineered ex vivo and then returned to the patient. In some embodiments, the therapy is for ALS. In some embodiments, the cell types may therefore be Astrocytes.

The treatment may comprise surgically implanting a composition of the invention into the human or animal body, for instance, near the liver.

Therapeutic compositions of the invention may advantageously improve the survival of therapeutic cells in the body.

The therapeutic composition of the invention is typically elongate, and can for example be cylinder-shaped, as this can facilitate delivery to tissue by injection or catheter. However, as will be discussed further below, the therapeutic composition may in principle be any shape. In some embodiments, it is generally not in the shape of a hollow tube.

The therapeutic composition may therefore have the shape of a polygonal prism. The polygonal prism may for instance be a triangular prism, a tetragonal prism, a pentagonal prism, a hexagonal prism, a heptagonal prism, an octagonal prism, a nonagonal prism, or a decagonal prism. The polygonal prism may for instance be a hexagonal prism. Often, the polygonal prism is a right prism which may for instance be a right triangular prism, a right tetragonal prism, a right pentagonal prism, a right hexagonal prism, a right heptagonal prism, a right octagonal prism, a right nonagonal prism, or a right decagonal prism. The polygonal prism may for instance be a right hexagonal prism. Often, the polygonal prism is a right regular prism, which may for instance be a right regular triangular prism, a right regular tetragonal prism, a right regular pentagonal prism, a right regular hexagonal prism, a right regular heptagonal prism, a right regular octagonal prism, a right regular nonagonal prism, or a right regular decagonal prism. The polygonal prism may for instance be a right regular hexagonal prism.

The therapeutic composition may have the shape of a cylinder or a polygonal prism. The polygonal prism may, for instance, be as further defined above, for instance it may be a right regular polygonal prism.

When the therapeutic composition has the shape of a cylinder or a polygonal prism, the height may, for instance, be from 5 mm to 10 cm. Often, the height of the cylinder or polygonal prism is from 8 mm to 8 cm, or for instance from 1 cm to 6 cm.

When the therapeutic composition has the shape of a cylinder or a polygonal prism, the diameter of the cylinder or polygonal prism is typically from 2 mm to 5 cm. The meaning of the diameter of a cylinder is well understood. The diameter of a polygon is also well understood, being the largest distance between any pair of vertices. Accordingly, the diameter of a polygonal prism is the largest distance between any pair of vertices on either of the polygonal faces of the prism. Thus, in the case of a hexagonal prism, and in particular in the case of a right regular hexagonal prism, the diameter is the diameter of either of the hexagonal faces of the prism, measured from a vertex (or intersection of two sides) of the hexagonal face, through the center of the face, to the opposite vertex of the face (where the two opposite sides of the face intersect).

The diameter of the cylinder or polygonal prism may for instance be from 4 mm to 3 cm, or for instance from 6 mm to 2 cm.

Advantageously, therapeutic compositions within the size, height and diameter ranges described herein are generally large enough to support cell growth which extend in all three dimensions enough to provide the benefits of a 3D cell culture versus a 2D layer of cells.

Electrospinning typically produces flat sheets of porous, nonwoven, fibrous, polymeric membranes. During the industrial production of such membranes these are generally collected on rotating drums, flat collectors or in a roll-to-roll fashion. In order for such a membrane to be used as an immunoprotective cell encapsulation device it needs to be shaped appropriately. This is achieved by either bonding two sheets or part of sheets together or folding part of one sheet onto itself. The bonding can be achieved by various techniques known in the art, such as laser welding (Weber, M., Hoheisel, A. & Glasmacher, B. (2016). "Automated control of the laser welding process of heart valve scaffolds" *Current Directions in Biomedical Engineering*, 2(1), pp. 301-305), sonic welding (Wirth, E. et al. "Preliminary Study of Ultrasonic Welding as a Joining Process for Electrospun Nanofibre Mats" *Nanomaterials* 8, 746 (2018)), thermal welding (You, Y., Won Lee, S., Jin Lee, S. & Park, W. H. "Thermal interfibre bonding of electrospun poly(L-lactic acid) nanofibers" *Mater. Lett.* 60, 1331-1333 (2006)), solvent bonding (Rianjanu, A., Kusumaatmaja, A., Suyono, E. A. & Triyana, K. "Solvent vapor treatment improves mechanical strength of electrospun polyvinyl alcohol nanofibers" *Heliyon* 4, e00592 (2018)), or gluing (Musiari, F. et al. "Feasibility study of adhesive bonding reinforcement by electrospun nanofibers" *Procedia Struct. Integr.* 2, 112-119 (2016)).

Furthermore, it is a well-known technique in the art to produce small-sized tubular structures of electrospun materials in the diameter range of several mm to cm (Krishnan, L. et al. "Vascularization and cellular isolation potential of a novel electrospun cell delivery vehicle" *J. Biomed. Mater. Res. A* 102, 2208-19 (2014)). A combination of the above mentioned bonding techniques and the production of small tubes can be used to form an enclosed therapeutic device for use in the invention.

After the electrospun material is produced, it may be cut into the desired size and shape. It may then be folded over, and stuck to itself (for instance, by sonic welding) to generate the final three dimensional product. Alternatively, two separate pieces of electrospun material can be fixed together by sonic welding to create a bag or pouch. Optionally, a further layer may be added to the final product, for instance, collagen fibers (for example in the form of a collagen membrane), which may surround the electrospun membrane to different degrees (for instance, it may partially or fully surround the electrospun membrane—e.g. it may surround by 60%, 80%, or 100%). The invention further provides a therapeutic composition comprising: (i) cells, a biomolecule or other active agent; and (ii) a scaffold. The biomolecule or other active agent may be a drug, a nucleic acid, a nucleotide, a protein, a polypeptide, an antibody, or an exosome. The nucleic acid may comprise DNA, RNA, RNAi, SaRNA or SiRNA. Optionally, the therapeutic composition comprises (i) cells, for instance adherent therapeutic cells, and (ii) a scaffold. The cells may be disposed within the porous network of fibers in the scaffold. The cells may be disposed in pores of the scaffold. The cells may be disposed on (e.g. may adhere to) the surface of the scaffold. The cells may be disposed in pores of the scaffold and may also be disposed on (e.g. may adhere to) the surface of the scaffold.

The polymer of the scaffold may be the same polymer as, or a different polymer from, the polymer of the fibers in the membrane. Often, it is the same polymer. In an embodiment of the invention, the scaffold can be formed of collagen, collagen fibers or collagen sponges.

Suitable polymers are discussed further hereinbelow.

In the therapeutic composition of the invention, the membrane may be disposed around at least part of the inner portion.

The invention also advantageously provides a device for the encapsulation of therapeutic cells and subsequent implantation into a subject's body and retrieval if necessary. This device is a preferred embodiment of the therapeutic composition according to the first aspect of this invention.

The device may preferably comprise: an encapsulated inner portion comprising a therapeutic agent; a barrier membrane layer (first layer), as disclosed herein, encapsulating the inner portion; and an outer layer (second layer) surrounding the barrier membrane layer.

Reference herein to the outer layer can also be understood to refer to the second layer.

The outer layer of the device may comprise one or more distinct layers.

The barrier membrane prevents implanted therapeutic cells from escaping into the patient and prevents the patients' immune cells from reaching the therapeutic cells.

The outer layer is typically a cell permeable material, for instance, a scaffold material, which allows vascularization adjacent to the inner, barrier membrane.

In a preferred embodiment, the outer layer comprises relatively large diameter (typically in the range 1000-10000 nm) electrospun fibers. The outer layer typically has a porosity, pore size and average fiber diameter which is greater than the membrane layer.

Preferably, the outer layer is formed from electrospun polyurethane fibers, and
  (i) The porosity is in the range 70% to 98%, preferably in the range 80% to 95%; and/or
  (ii) The average pore diameter is in the range 5 to 80 µm, preferably in the range 10 to 50 µm; and/or
  (iii) the mean diameter of the polymer fibers is in the range 1 to 10 µm, preferably in the range 2 to 8 µm, most preferably in the range 3 to 7 µm.

Preferably the outer layer is formed from fibers, preferably electrospun polyurethane fibers. The outer layer may be resorbable or nonresorbable. Alternatively, the outer layer may be a hydrogel. In a further aspect it may comprise decellularized tissue.

The inner portion optionally comprises a carrier material together with the therapeutic agent. This material could be the scaffold material discussed above in relation to the therapeutic composition. The inner portion material could be fibrous in nature, for instance, an electrospun polyurethane fiber. Alternatively, it could be a hydrogel, a foam, or a tissue alginate, gelatin, or collagen (optionally fibers or sponges), or decellularized tissue.

Preferably, the inner portion (including any carrier or scaffold) and/or outer layer (i.e. the second layer) may comprise a material formed from fibers. Such fibers typically comprise a biocompatible polymer. Any suitable biocompatible polymer can be employed, and the biocompatible polymer may for instance be a natural polymer or a synthetic polymer. In some embodiments, the polymer is a bioerodible or biodegradable polymer.

The fibers of the inner portion (including any carrier or scaffold) and/or outer layer (i.e. the second layer) in the preceding paragraph may for instance comprise any of the following polymers: poly(L-lactide); poly(glycolic acid); polyhydroxybutyrate; polystyrene; polyethylene; polypropylene; poly(ethylene oxide); a poly(ester urethane); poly (vinyl alcohol); polyacrylonitrile; polylactide; polyglycolide; polyurethane; polycarbonate; polyimide; polyamide; aliphatic polyamide; aromatic polyamide; polybenzimidazole; poly(ethylene terephthalate), poly[ethylene-co-(vinyl acetate)]; poly(vinyl chloride); poly(methyl methacrylate); poly(vinyl butyral); poly(vinylidene fluoride); poly(vinylidene fluoride-co-hexafluoropropylene); cellulose acetate; poly(vinyl acetate); poly(acrylic acid); poly(methacrylic acid); polyacrylamide; polyvinylpyrrolidone; poly (phenylene sulfide); hydroxypropylcellulose; polyvinylidene chloride, polytetrafluoroethylene, a polyacrylate, a polymethacrylate, a polyester, a polysulfone, a polyolefin, polysilsesquioxane, silicone, epoxy, cyanate ester, a bismaleimide polymer; polyketone, polyether, polyamine, polyphosphazene, polysulfide, an organic/inorganic hybrid polymer or a copolymer thereof, for instance, poly(lactide-co-glycolide); polylactide-co-poly(F-caprolactone) or poly (L-lactide)-co-poly(F-caprolactone); or a blend thereof, for instance a blend of poly(vinyl alcohol) and poly(acrylic acid).

The fibers in may comprise a bioerodible or biodegradable polymer, for instance a polymer selected from poly(L-lactide); poly(glycolic acid); polyhydroxybutyrate; and poly (ester urethanes).

The fibers may alternatively for instance comprise a biopolymer, or a blend of a biopolymer with a synthetic polymer. The following biopolymers and blends of biopolymers with synthetic polymers may for instance be used: collagen; collagen/poly(ethylene oxide); collagen/poly(F-caprolactone); collagen/polylactide-co-poly(F-caprolactone); gelatin; gelatin/poly(F-caprolactone); gelatin/poly (ethylene oxide); casein/poly(vinyl alcohol); casein/poly (ethylene oxide); lipase; cellulase/poly(vinyl alcohol); bovine serum albumin/poly(vinyl alcohol); luciferase/poly (vinyl alcohol); β-chymotrypsin; fibrinogen; silk; regenerated silk; regenerated *Bombyx mori* silk; *Bombyx mori* silk/poly(ethylene oxide); silk fibroin; silk fibroin/chitosan; silk fibroin/chitin; silk/poly(ethylene oxide) (coaxial); artificial spider silk; chitin; chitosan; chitosan/poly(ethylene oxide); chitosan/poly(vinyl alcohol); quaternized chitosan/poly(vinyl alcohol); hexanoylchitosan/polylactide; cellulose; or cellulose acetate.

The fibers may alternatively for instance comprise a blend of two or more polymers, a copolymer (which may for instance be a block copolymer), or a blend of a polymer with an inorganic material.

Nonlimiting examples of such blends blend of two or more polymers include a polyvinylpyrrolidone/polylactide blend; a polyaniline/polystyrene blend; a polyaniline/poly (ethylene oxide) blend; a poly(vinyl chloride)/polyurethane blend, a poly[(m-phenylene vinylene)-co-(2,5-dioctyloxy-p-phenylene vinylene)]/poly(ethylene oxide) blend; a poly[2-methoxy-5-(2'-ethylhexyloxy)-1,4-phenylene vinylene] (MEH-PPV)/polystyrene blend, a polyaniline/polystyrene blend; a polyaniline/polycarbonate blend, a poly(ethylene terephthalate)/poly(ethylene terephthalate)-co-poly(ethylene isophthalate) blend, a polysulfone/polyurethane blend; a chitosan/polylactide blend, a polyglycolide/chitin blend, and a polylactide/poly(lactide-co-glycolide) blend.

Nonlimiting examples of such block copolymers systems include polylactide-b-poly(ethylene oxide) block copolymers; poly(lactide-co-glycolide)-b-poly(ethylene oxide) block copolymers; poly[(trimethylene carbonate)-b-(ε-caprolactone)] block copolymers; polystyrene-b-polydimethylsiloxane and polystyrene-b-polypropylene block copolymers; polystyrene-b-polybutadiene-b-polystyrene block copolymers and polystyrene-b-polyisoprene block copolymers.

Thus, the nanofibers may for instance comprise any of the materials listed in the preceding paragraphs. Scaffolds of nanofibers comprising the above polymers, copolymers, and blends two or more polymers, can be produced by electrospinning, as detailed in in Greiner and Wendorff, *Angew. Chem. Int. Ed.* 2007, 46, 5670-5703.

The therapeutic composition or device of the invention may further comprise additives, preferably mixed with the fibers of electrospun material. Such additives may include growth factors such as VEGF. An additive may alternatively be an oxygen-releasing material such as $CaO_2$ or hemoglobin. Since a significant problem with Islet transplantation is the early death of the islets due to hypoxic conditions, having an oxygen releasing agent can address hypoxia. Alternative additives include crosslinking agents. For instance, calcium ions for the crosslinking of hydrogels. Suitable additives may be selected from the following: Hemoglobin, Peroxides (for instance, $H_2O_2$, $CaO_2$, $MgO_2$, $Li_2O_2$, $Na_2O_2$), Sodium Percarbonate ($Na_2CO_3$), Perfluorocarbons, Hydroxyapatite, Tricalcium phosphate (bone growth promoting materials), Growth factors, Catalase, and other enzymes. Other additives my include, in some embodiments, antimicrobials, antivirals, antifungals, and/or silver nanoparticles.

Examples of Growth factors may include any one or more of the following: Colony Stimulating Factors (m-CSF, G-CSF, GM-CSF), Epidermal growth factor (EGF), Erythropoietin (EPO), Fibroblast growth factor (FGF), Hepatocyte growth factor (HGF), Hepatoma-derived growth factor (HDGF), interleukins, Keratinocyte growth factor (KGF), Migration-stimulating factor (MSF), Macrophage-stimulating protein (MSP), also known as hepatocyte growth factor-like protein (HGFLP), Myostatin (GDF-8), Neuregulins (e.g. Neuregulin 1, 2, 3, or 4), Neurotrophins (e.g. Brain-derived neurotrophic factor (BDNF), Nerve growth factor (NGF), Neurotrophin-3 or -4), Placental growth factor (PGF), Platelet-derived growth factor (PDGF), Renalase (RNLS), T-cell growth factor (TCGF), Thrombopoietin (TPO), Transforming growth factors such as Transforming growth factor-alpha (TGF-α) or -beta (TGF-β), Tumor necrosis factor-alpha (TNF-α), Vascular endothelial growth factor (VEGF) or factors involved in the Wnt Signaling Pathway.

In particular, the growth factor may be Insulin and/or an Insulin-like growth factor. Also preferred are Cytokines including the interleukins mentioned above.

The additive may be present in any of the component layers of the composition or device of the invention. It is preferably present in the outer and/or inner portion.

Often, the cells in the therapeutic composition or device of the invention comprise adherent therapeutic cells. Adherent cells are cells which are capable of adhering to culture vessels which have been specifically treated for the culture of adherent cells. The concept of adherent cells is well known to a person skilled in the art. The skilled person is capable of identifying whether or not cells are adherent. Therapeutic cells are cells which are capable of having a therapeutic effect. Therapeutic cells are typically living cells. Therapeutic cells are typically cells which are capable of repairing damaged or diseased tissue. The therapeutic cells are preferably autologous. In other words, the cells are preferably derived from the patient into which the cells will be administered to repair damaged or diseased tissue. Alternatively, the cells are preferably allogeneic. In other words, the cells are preferably derived from a patient that is immunologically compatible with the patient into which the cells will be administered to repair damaged or diseased tissue. The cells may be semiallogeneic. Semiallogeneic populations are typically produced from two or more patients that are immunologically compatible with the patient into which the cells will be administered. In other words, all of the cells are preferably genetically identical with the patient into which they will be administered or sufficiently genetically identical that the cells are immunologically compatible with the patient into which they will be administered.

The composition typically comprises more than one cell, such at least about 2, at least about 5, at least about 10, at least about 20, at least about 30, at least about 40, at least about 50, at least about 100, at least about 200, at least about 500, at least about 1000, at least about 2000, at least about 5000, at least about 10000, at least about 50000, at least about 100000, at least about $2 \times 10^5$, at least about $5 \times 10^5$, at least about $1 \times 10^6$, at least about $2 \times 10^6$, at least about $5 \times 10^6$, at least about $1 \times 10^7$, at least about $2 \times 10^7$, at least about $5 \times 10^7$, at least about $1 \times 10^8$ or at least about $2 \times 10^8$ cells. In some instances, the composition may comprise at least $1.0 \times 10^7$, at least $1.0 \times 10^8$, at least $1.0 \times 10^9$, at least $1.0 \times 10^{10}$, at least $1.0 \times 10^{11}$ or at least $1.0 \times 10^{12}$ cells or even more cells.

The number of cells in the composition typically depends on the size of the shape. The number of cells is often from about $0.5 \times 10^5$ to about $3 \times 10^5$, such as from about $1 \times 10^5$ to about $2 \times 10^5$, particularly in a scaffold of the invention, which is cylinder-shaped, and has a length of from about 4 mm to about 8 mm, and a diameter of from about 200 μm to about 500 μm.

The adherent therapeutic cells may comprise pancreatic R cells, for instance, beta cell aggregates. A beta cell aggregate is a conglomeration of two or more cells, at least one of which is a beta cell. An example of a beta cell aggregate is an islet of Langerhans. An islet of Langerhans may for example be isolated from cadaveric donor pancreata.

The invention provides a process of manufacturing of barrier membrane, therapeutic composition, or device of the invention. In a preferred embodiment, a biocompatible membrane may be produced as a sheet membrane through electrospinning. Such a sheet membrane may then easily be shaped into a final therapeutic composition or device.

Alternatively, membranes of the invention could be incorporated into the coating of an existing structure with any combination of these layers and the subsequent sealing with, sonic welding, heat sealing, solvent bonding, gluing, laser welding, etc.

Suitable methods for manufacturing nanofiber nonwoven fabrics are disclosed in US 2012-0115386 A1.

The invention additionally provides a process for producing a therapeutic composition of the invention as defined herein, comprising combining (i) a scaffold and (ii) cells, a biomolecule or other active agent, in a culture vessel. Both (i) the scaffold, and (ii) the cells, biomolecule, or other active agent, may be as further defined anywhere herein.

In one embodiment, the process for producing a therapeutic composition of the invention comprises combining (i) a scaffold and (ii) adherent therapeutic cells, a drug, a nucleic acid, a nucleotide, a protein, a polypeptide, or an exosome in a culture vessel.

The process for producing a therapeutic composition of the invention may for instance comprise: (i) combining a scaffold and (ii) allowing the adherent therapeutic cells to infiltrate and proliferate on the surface and within the outer portion of the scaffold and thereby producing said therapeutic composition.

The number of the cells added to the vessel typically corresponds to the number of cells which should be present in the composition of the invention. The proportion of added cells which attach to the scaffold can be measured by removing the scaffold from the vessel and determining how many, if any, cells remain in the vessel. Techniques for culturing cells are well known to a person skilled in the art.

The scaffold and cells may be combined in any suitable culture vessel. The vessel may be a flask or a well of a flat plate, such as a standard 6-well, 24-well or 96-well plate. Such flasks and plates are commercially available from Corning, Fisher scientific, VWR suppliers, Nunc, Starstedt, or Falcon.

The invention further provides a therapeutic composition of the invention for use in a method for treatment of the human or animal body by therapy.

In all instances, the therapeutic cells are preferably derived from the patient or an allogeneic donor. Deriving the cells from the patient should ensure that the cells are themselves not rejected by the patient's immune system. Any difference between the donor and recipient will ultimately cause clearance of the cells, but not before they have repaired at least a part of the damaged or diseased tissue.

The therapeutic composition of the invention may be administered to any suitable patient. The patient is generally a human patient. The patient may be an infant, a juvenile or an adult. The patient may be known to have a damaged or diseased tissue or is suspected of having a damaged or diseased tissue. The patient may be susceptible to, or at risk from, the relevant disease or injury. The patient may have diabetes.

The transfection of cells is well known in the art. The cells are typically transfected with a nucleic acid encoding the agent. For instance, viral particles or other vectors encoding the agent may be employed.

The nucleic acid gives rise to expression of the agent in the cells. The nucleic acid molecule will preferably comprise a promoter which is operably linked to the sequences encoding the agent and which is active or which can be induced in the cells.

The composition may be administered by any route. Suitable routes include, but are not limited to, intravenous, intramuscular, intraperitoneal, or other appropriate administration routes. The composition is preferably administered directly to the damaged or diseased tissue. By injection or insertion via a catheter are particularly preferred.

As mentioned above, the membrane of the invention is formed by electrospinning. Preferably, any scaffolds used in the invention are also produced by electrospinning.

In a preferred embodiment of the invention, there is provided a process for producing a biocompatible porous membrane comprising electrospinning a fiber (preferably, a nanofiber) precursor solution onto a collection substrate to produce a biocompatible membrane comprising a nonwoven network of thermoplastic polyurethane polymer fibers; wherein the nanofiber precursor solution comprises a polymer dissolved in a solvent.

The network of polymer fibers can comprise a single layer of fibers or multiple (two or more) layers. The porosity of the layers and the pore size within each layer may be the same or different.

The electrospinning process can easily be adapted to produce membranes having multilayered structures. The production of multilayered structures is discussed further below.

Thus the membrane according to the first aspect of this invention may have a gradient structure. By this is meant that at least one characteristic of the membrane (for instance, density, solidity, porosity, fiber size, pore size) varies on passing through the body of the membrane, from one side to the other. The characteristics are varied by altering conditions during the electrospinning process.

A typical multilayered membrane comprises a bilayer structure, as described herein. When the membrane is combined with a scaffold, it is preferred in some embodiments that the layer with the smaller average pore diameter contacts the scaffold. This then forms a trilayer structure, together with the scaffold.

The polymer fibers in the membrane are produced by electrospinning, as detailed further below. Fibers forming the scaffold (as further discussed below) may also be formed by electrospinning, or by other suitable methods which are known to the skilled person including, but not limited to, melt spinning, dry spinning, wet spinning, and extrusion. Electrospinning is preferred.

The use of electrospinning offers certain advantages. For instance, there can be batch-to-batch reproducibility, and compatibility with current automation equipment. Furthermore, polymer (nano)fibers with specific mean fiber diameters and low standard deviations from the mean can be produced very consistently. This provides control over porosity and pore size.

The polymer fibers of the membrane and the scaffold may comprise the same polymer as or a different polymer. If they are the same polymer, the polymer is polyurethane.

The fibers of the scaffold may be the same or different from the fibers of the inner and/or outer portion. In some embodiments, the scaffold fibers are the same as the fibers of the inner portion. In some embodiments, the scaffold fibers are the same as the fibers of the outer portion (if those outer portion fibers are different from the inner portion fibers. For example, the scaffold typically comprises, or for instance consists of, a polymer which is both bioabsorbable and biocompatible, for instance poly(lactide), poly(glycolide), poly(lactide-co-glycolide) (PLGA) or polycaprolactone (PCL). Polyhydroxybutyrate or a poly(ester urethane) may alternatively be employed.

More generally, the fibers of the scaffold may be selected from the following: poly(lactide); poly(glycolide); poly(lactide-co-glycolide) (PLGA); polycaprolactone (PCL); polyhydroxybutyrate; poly(F-caprolactone); polystyrene; polyethylene; polypropylene; poly(ethylene oxide); a poly(ester urethane); poly(vinyl alcohol); polyacrylonitrile; polylactide; polyglycolide; polyurethane; polycarbonate; polyimide; polyamide; aliphatic polyamide; aromatic polyamide; polybenzimidazole; poly(ethylene terephthalate); poly[ethylene-co-(vinyl acetate)]; poly(vinyl chloride); poly(methyl methacrylate); poly(vinyl butyral); poly(vinylidene fluoride); poly(vinylidene fluoride-co-hexafluoropropylene); cellulose acetate; poly(vinyl acetate); poly(acrylic acid); poly(methacrylic acid); polyacrylamide; polyvinylpyrrolidone; poly(phenylene sulfide); hydroxypropylcellulose; polyvinylidene chloride, polytetrafluoroethylene, a polyacrylate, a polymethacrylate, a polyester, a polysulfone, a polyolefin, polysilsesquioxane, silicone, epoxy, cyanate ester, a bis-maleimide polymer; polyketone, polyether, polyamine, polyphosphazene, polysulfide, an organic/inorganic hybrid polymer or a copolymer thereof, for instance, poly(lactide-co-glycolide); polylactide-co-poly(F-caprolactone) or poly(L-lactide)-co-poly(F-caprolactone); or a blend thereof, for instance a blend of poly(vinyl alcohol) and poly(acrylic acid).

In some embodiments, the scaffold may comprise collagen in the form of fibers or as a collagen sponge. The collagen scaffold is useful due to the high biocompatibility of collagen. Alternatives to collagen, that may be used in some embodiments, include the polymers listed above and the bioerodible or biodegradable polymers below.

The fibers of the scaffold may independently comprise, or consist of, a bioerodible or biodegradable polymer, for instance a polymer selected from poly(lactide), poly(glycolide), poly(lactide-co-glycolide) (PLGA), polycaprolactone (PCL), poly(F-caprolactone) (PCL), polyhydroxybutyrate and poly(ester urethanes).

The fibers of the scaffold may alternatively for instance independently comprise, or consist of, a biopolymer, or a blend of a biopolymer with a synthetic polymer.

The membrane according to the first aspect of the invention may comprise a plurality of layers. For instance, the membrane may comprise 1, 2, 3, 4 or 5 distinct layers. The layers may comprise different levels of porosity.

Typically, the plurality of layers in the membrane of the invention has a thickness (depth) of from about 30 µm to about 1000 µm. The plurality of layers in the membrane may for instance have a thickness (depth) of from about 30 µm to about 800 µm, for instance from about 40 µm to about 600 µm, or from about 50 µm to about 400 µm, or 50 µm to 200 µm or 50 µm to 150 µm. The plurality of layers in the membrane may for example have a thickness (depth) of from about 50 µm to about 200 µm, or for instance from about 80 µm to about 120 µm.

The porosity and pore size of each layer in the membrane may be as defined above for the membrane according to the first aspect of the invention. Thus, each layer may, independently, have a porosity of equal to or greater than 50%. Further, each layer of the membrane, may, independently, have a mean pore size of from 10 µm to 20 µm.

The process of electrospinning per se is well known and is described for instance in the following review articles: Z.-M. Huang et al., *Composites Science and Technology* 63 (2003) 2223-2253 and in Greiner and Wendorff, *Angew. Chem. Int. Ed.* 2007, 46, 5670-5703. The skilled person will know how to suitably apply this technique. It is briefly discussed below.

The process of electrospinning typically involves electrospinning a fiber precursor solution onto a collection substrate, or onto a preceding layer on the collection substrate, while rotating the collection substrate at a particular speed, wherein the fiber precursor solution comprises a particular desired polymer dissolved in a solvent.

Typically, in carrying out electrospinning, a polymer or polymer blend from which the fibrous network is to be produced is dissolved in an appropriate solvent until a homogeneous solution of the required concentration is obtained. The concentration of the polymer solution must generally be high enough to achieve adequate chain entanglements in order for a continuous fiber to be formed. The polymer solution is typically then loaded into a vessel, usually a syringe, connected to a conductive (typically metal) capillary. The capillary is connected to a high voltage (usually to the positive terminal of a high voltage DC power supply), at a fixed distance from an earthed collection device. The collection device may be metallic and is typically covered in a collection substrate onto which the fibers are deposited. The collection device is preferably rotatable, to ensure uniform deposition of the material. Fibers are typically produced by passing the polymer solution at a fixed flow rate through the metal capillary whilst applying a high voltage to the capillary in order to establish an electric field between the capillary and the collection device. The applied voltage should be high enough to overcome the surface tension of the polymer droplet at the tip of the capillary. As the charge builds at the surface of the droplet, the surface area has to increase to accommodate the additional charge, this occurs through the formation of a Taylor Cone from the droplet, from which a continuous fiber is extracted. As the fiber travels toward the grounded collector, the solvent rapidly evaporates, and the fiber is further elongated due to instabilities arising from the columbic repulsions of the surface charges on the jet. The instabilities in the jet resulting from the high charge density cause the jet to whip about rapidly resulting in a nano/micro diameter solid (dry) filament. The collector is rotated slowly (e.g. at a rate of around 100 RPM) if a random, nonwoven fibrous layer on the substrate is desired. Alternatively, the collector may be rotated at a higher speed (e.g. at a rate of around 2500 RPM) if a layer of aligned fibers is desired. A plurality of layers of different fiber alignments, ranging from randomly orientated nonwoven layers to layers of highly aligned fibers, may be deposited by changing the rotation speed during the deposition. After a fixed amount of material has been deposited to generate a layer or plurality of layers of a particular desired thickness, the layer or plurality of layers is dried in order to remove any residual solvent/moisture from the fibers. Typically, it is dried under vacuum, for instance for 24-48 hours at room temperature (approx. 25° C.).

Any suitable polymer may be employed in the fiber precursor solution or solutions used in the electrospinning process. The polymer employed may be any of the polymers listed above in relation to the membrane or the scaffold. All of those polymers can be used in an electrospinning process to produce a porous three-dimensional network of nanofibers, as detailed in Greiner and Wendorff, *Angew. Chem. Int. Ed.* 2007, 46, 5670-5703.

Any suitable solvent may be employed in the nanofiber precursor solution. A wide range of solvents can be used in electrospinning, including for instance water and polar, nonpolar, protic, and aprotic organic solvents. The solvent is chosen to suit the polymer or blend employed, particularly so that a homogeneous solution of the required concentration of the polymer can be obtained.

The concentration of the polymer in the solution should be high enough to achieve adequate chain entanglements in order for a continuous fiber to be formed. Typically, the concentration of the polymer in said solvent is from about 1 wt. % to about 20 wt. %. The concentration of the polymer in said solvent may for instance be from about 2 wt. % to about 10 wt. %. For instance, the concentration of the polymer in said solvent may be about 3 wt. %, to about 5 wt. %.

Typically, the dispensing capillary of the fiber forming module has an inner diameter of from about 0.5 mm to about 1.0 mm.

In order to ensure uniform deposition on the collection substrate, the electrospinning typically further comprises moving at least a portion of the fiber collection device relative to the fiber forming module during said deposition. Thus, usually, the electrospinning further comprises moving at least a portion of the fiber collection device during said deposition.

Deposition of the plurality of layers on the collection substrate is continued until a plurality of layers of a particular desired thickness has been obtained. This thickness of the plurality of layers may be as further defined hereinbefore for the membrane of the invention and may for instance be from about 30 μm to about 1000 μm, or for instance from about 50 μm to about 200 μm or 150 μm, for example from about 80 μm to about 120 μm.

Thus, typically the step of feeding said fiber precursor solution through the dispensing capillary whilst applying said voltage is performed until the thickness of the plurality of layers of the scaffold precursor has the appropriate thickness.

Typically, the flow rate at which the fiber precursor solution is fed through the dispensing capillary is from 100 μL/h to 3000 L/h. More typically, it is from 400 μL/h to 2500 μL/h, for instance about 2000 μL/h.

The distance between the dispensing capillary and the collection substrate is typically from 200 mm to 400 mm. More typically, it is from 200 mm to 300 mm, for instance about 250 mm.

The voltage applied across the dispensing capillary and the fiber collection device is typically from 2 kV to 15 kV. More typically, it is from 4 kV to 10 kV, for instance about 5-8 kV.

Usually, the electrospinning is performed at a temperature of from 22° C. to 28° C. More typically, the electrospinning is performed at a temperature of from 23° C. to 27° C., for instance about 25° C.

Typically, the electrospinning is performed in air having a relative humidity of from 20% to 45%. The electrospinning may for instance be performed in air having a relative humidity of 35% to 45%, for instance about 40%.

The electrospinning process, of producing the membrane or scaffold may further comprise: drying the plurality of layers of polymer fibers thus produced to remove residual solvent; and cutting the plurality of layers of polymer fibers into an elongate strip and thereby producing said scaffold precursor. Typically, the scaffold precursor is dried under vacuum. Typically, the drying is done at room temperature under vacuum.

Typically, the electrospinning process further comprises: removing the membrane or scaffold thus produced from the collection substrate. The collection substrate typically comprises a release paper sheet, aluminum foil, or a silicone-coated sheet.

The invention may also be defined by the following further aspects:

Also provided in a further aspect of the present invention is a therapeutic composition comprising an inner portion and a biocompatible membrane fully or partially surrounding the inner portion; wherein the biocompatible membrane comprises a porous, nonwoven network of thermoplastic polyurethane polymer fibers formed by electrospinning.

The membrane described above can be formulated to act as a cell encapsulation device, selectively allowing the passage of agents such as nutrients, but not cells.

Also provided in a further aspect of the present invention is a membrane comprising at least two layers, wherein:
(i) the first layer is a biocompatible membrane comprising a porous, nonwoven network of thermoplastic polyurethane polymer fibers formed by electrospinning; and
(ii) the second layer is disposed on the first layer.

Also provided in a further aspect of the present invention is a biocompatible membrane comprising a porous, nonwoven network of thermoplastic polyurethane polymer fibers formed by electrospinning; for use in a method of immunoprotecting therapeutic cells.

Also provided in a further aspect of the present invention is a membrane or therapeutic composition as defined above for use in a method of treatment of the human or animal body by therapy.

Also provided in a further aspect of the present invention is a process for producing a therapeutic composition according to the first aspect of the invention comprising:
(i) an electrospinning process to produce a biocompatible membrane comprising a porous, nonwoven network of thermoplastic polyurethane polymer fibers; and
(ii) molding the biocompatible membrane to produce a therapeutic composition in which an inner portion is fully or partially surrounded.

The following applies to any aspects of the invention, unless otherwise apparent.

In some embodiments, the biocompatible membrane has a porosity of greater than or equal to 50%, preferably in the range 50% to 80%.

In some embodiments, the biocompatible membrane has an average pore diameter of less than 5 μm and the average pore diameter is preferably less than 2 μm.

In some embodiments, the biocompatible membrane has a thickness in the range 10 to 250 μm, preferably in the range 10 to 150 μm or 20 to 150 μm, most preferably in the range 50 to 150 μm or 50 to 200 μm.

In some embodiments, the mean diameter of the polymer fibers is less than 700 nm, preferably less than 600 nm, preferably less than 500 nm and is most preferably in the range 100-500 nm, even more preferably in the range 50-500 nm.

In some embodiments, the biocompatible membrane is nonbiodegradable.

In some embodiments, the biocompatible membrane comprises a bilayered structure. In some embodiments, the bilayer is arranged such that the layer with the higher porosity is inwards facing, for example toward a wound site, and lower porosity layer is outward facing to prevent the passage for bacteria and particulates, for example, into the wound site, whilst preferably still allowing oxygen and/or water into the wound site. This arrangement may be useful, for example, in internal wound care, e.g. periodontitis, nerve sheaths, hernia repair patches, synthetic periosteum membrane, and/or fistula. As such, a corresponding internal wound care device is also provided. This may also include any of the additives described herein.

In some embodiments, the composition further comprises a therapeutic agent, wherein the therapeutic agent is preferably in the inner portion, and preferably wherein the therapeutic agent is selected from therapeutic cells, a drug, a nucleic acid, a nucleotide, a protein, a polypeptide, an antibody, a particle such as lipid nanoparticle, an extracellular vesicle or exosome, optionally wherein the nucleic acid comprises DNA, RNA, RNAi, SaRNA or SiRNA.

In some embodiments, the composition further comprises a carrier on or in which the therapeutic agent is disposed, preferably wherein the therapeutic agent is attached to the surface of a carrier, disposed in pores of the carrier, or both.

In some embodiments, the biocompatible membrane fully or partially surrounds the carrier.

In some embodiments, the carrier comprises a porous, nonwoven network of polymer fibers or a hydrogel, gelatin, collagen sponges or decellularized tissue.

In some embodiments, the composition comprises cells, wherein the cells are preferably pancreatic β cells or islet cells.

In some embodiments, the composition further comprises an outer layer disposed on an outer surface of the biocompatible membrane, preferably wherein the outer layer is formed from electrospun fibers, preferably polyurethane fibers, and/or comprises a hydrogel, gelatin or collagen sponges, or decellularized tissue.

In some embodiments, the outer layer has a porosity which is higher than the porosity of the biocompatible membrane, and/or wherein the mean average fiber diameter of the outer layer is greater than the mean average fiber diameter in the biocompatible membrane, and/or wherein the average pore diameter of the outer layer is greater than the average pore diameter of the inner layer.

In some embodiments, the outer layer is formed from electrospun polyurethane fibers, and:
 (i) The porosity is in the range 70% to 98%, preferably in the range 80% to 95%; and/or
 (ii) The average pore diameter is in the range 5 to 80 μm, preferably in the range 10 to 50 μm; and/or
 (iii) the mean diameter of the polymer fibers is in the range 1 to 10 μm, preferably in the range 2 to 8 μm, most preferably in the range 3 to 7 μm.

In some embodiments, the composition further comprises one or more additives, wherein the additives are preferable disposed within the carrier or outer layer (if present), further wherein the additives are selected from growth factors such as VEGF, crosslinking agents, Growth factors, Catalase and other enzymes; or an oxygen-releasing material such as $CaO_2$ or Hemoglobin, Peroxides (for instance, $H_2O_2$, $CaO_2$, $MgO_2$, $Li_2O_2$, $Na_2O_2$), Sodium Percarbonate ($Na_2CO_3$), Perfluorocarbons, Hydroxyapatite, Tricalcium phosphate (bone growth promoting materials), most preferably $CaO_2$ and/or $MgO_2$ which may act as a crosslinking agent in a alginate hydrogel; catalase is also preferred in combination with an oxygen-releasing material which advantageously mops up any toxic hydrogen peroxide released.

Also provided in a further aspect of the present invention is a membrane comprising at least two layers, wherein (i) the first layer is a biocompatible membrane comprising a porous, nonwoven network of thermoplastic polyurethane polymer fibers formed by electrospinning; and (ii) the second layer is disposed on the first layer. In some embodiments, the first layer is as defined as a biocompatible membrane having a porosity of greater than or equal to 50%, preferably in the range 50% to 80%; having an average pore diameter of less than 5 μm; having a thickness in the range 10 to 150 μm, preferably in the range 20 to 150 μm, most preferably in the range 50 to 150 μm or 50 to 200 μm; or where the mean diameter of the polymer fibers is less than 700 nm, preferably less than 600 nm, preferably less than 500 nm and is most preferably in the range 100-500 nm, even more preferably in the range 50-500 nm. In some embodiments, the second layer further comprises an outer layer which is disposed on an outer surface of the biocompatible membrane, preferably wherein the outer layer is formed from electrospun fibers, preferably polyurethane fibers, and/or comprises a hydrogel, gelatin or collagen sponges, or decellularized tissue; which has a porosity which is higher than the porosity of the biocompatible membrane, and/or wherein the mean average fiber diameter of the outer layer is greater than the mean average fiber diameter in the biocompatible membrane, and/or wherein the average pore diameter of the outer layer is greater than the average pore diameter of the inner layer; and where it is formed from electrospun polyurethane fibers, and (i) the porosity is in the range 70% to 98%, preferably in the range 80% to 95%; and/or (ii) the average pore diameter is in the range 5 to 80 μm, preferably in the range 10 to 50 μm; and/or (iii) the mean diameter of the polymer fibers is in the range 1 to 10 μm, preferably in the range 2 to 8 μm, most preferably in the range 3 to 7 μm. In some embodiments, the membrane further comprises one or more additives, wherein the additives are preferably selected from growth factors such as VEGF, crosslinking agents, Growth factors, Catalase and other enzymes; or an oxygen-releasing material such as $CaO_2$ or Hemoglobin, Peroxides (for instance, $H_2O_2$, $CaO_2$, $MgO_2$, $Li_2O_2$, $Na_{2O2}$), Sodium Percarbonate ($Na_2CO_3$), Perfluorocarbons, Hydroxyapatite, Tricalcium phosphate (bone growth promoting materials), most preferably $CaO_2$ and/or $MgO_2$ which may act as a crosslinking agent in a alginate hydrogel; catalase is also preferred in combination with an oxygen-releasing material which advantageously mops up any toxic hydrogen peroxide released.

EXAMPLES

The present invention is further illustrated in the Examples which follow.

Example 1

A thermoplastic aromatic polycarbonate-based polyurethanes (PU) (Chronoflex, Advansource, US) was used in the manufacture of the device precursor/membranes by electrospinning. A solution containing 5.0 wt. % of PU or 25 wt. % in Hexafluoro-2-propanol (HFIP) (Sigma Aldrich, UK) was prepared.

The device precursor contained two distinct layers of electrospun fiber, a nonwoven top and bottom layer. The electrospun scaffold precursors were prepared by delivering the polymer solution at a constant feed rate $8.333 \times 10^{-7}$ L/s for both the bottom and the top layer via a syringe pump and was electrospun vertically with an accelerating voltage of +5 kV DC-+8 kV. Temperature and relative humidity were kept constant (respectively at 25° C. and 40% RH) in a climate-controlled electrospinning machine (LE-100, Bionicia, Spain). Fibers were collected on release paper sheets wrapped around a rotating collector positioned 20 cm from the tip of the needle. The collector was rotated at 200 RPM when preparing the top and bottom nonwoven layers. Longitudinal translation was also applied, using a programmable motorized stage with a translation speed of 40 mm/s. Electrospinning was performed for 270 minutes to fabricate the desired sheet thickness, i.e. the desired thickness for the device precursor.

Fiber diameter and scaffold morphology characterization were performed by scanning electronic microscopy (SEM) (Phenom G2 Pro equipped with FiberMetric software, Phenom World, the Netherlands), using automated image characterization of multiple images in order to determine the mean fiber diameter and the relative standard deviation. The FiberMetric software automatically identifies the location of the fibers within the captured SEM image and measures the diameter of each fiber 20 times at a specific location. Typically, around 100 of such measurements are performed per image. The diameter of the fibers can alternatively be obtained via manual measurements/analysis of multiple SEM images.

The average fiber diameter of the fibers on the bottom layer was 600 nm with a tolerance of 30%. The average fiber diameter of the fibers on the top layer was 5 µm with a tolerance of 40%. Thickness of the sheet is measured using a micrometer. The target average thickness of the material was 150 µm with a tolerance of 20%.

The fibrous mat was dried in a vacuum oven at ~10 mBar for over 24 hours at 25° C. to reduce the amount of residual solvent remaining from the fabrication process.

Figure 2:
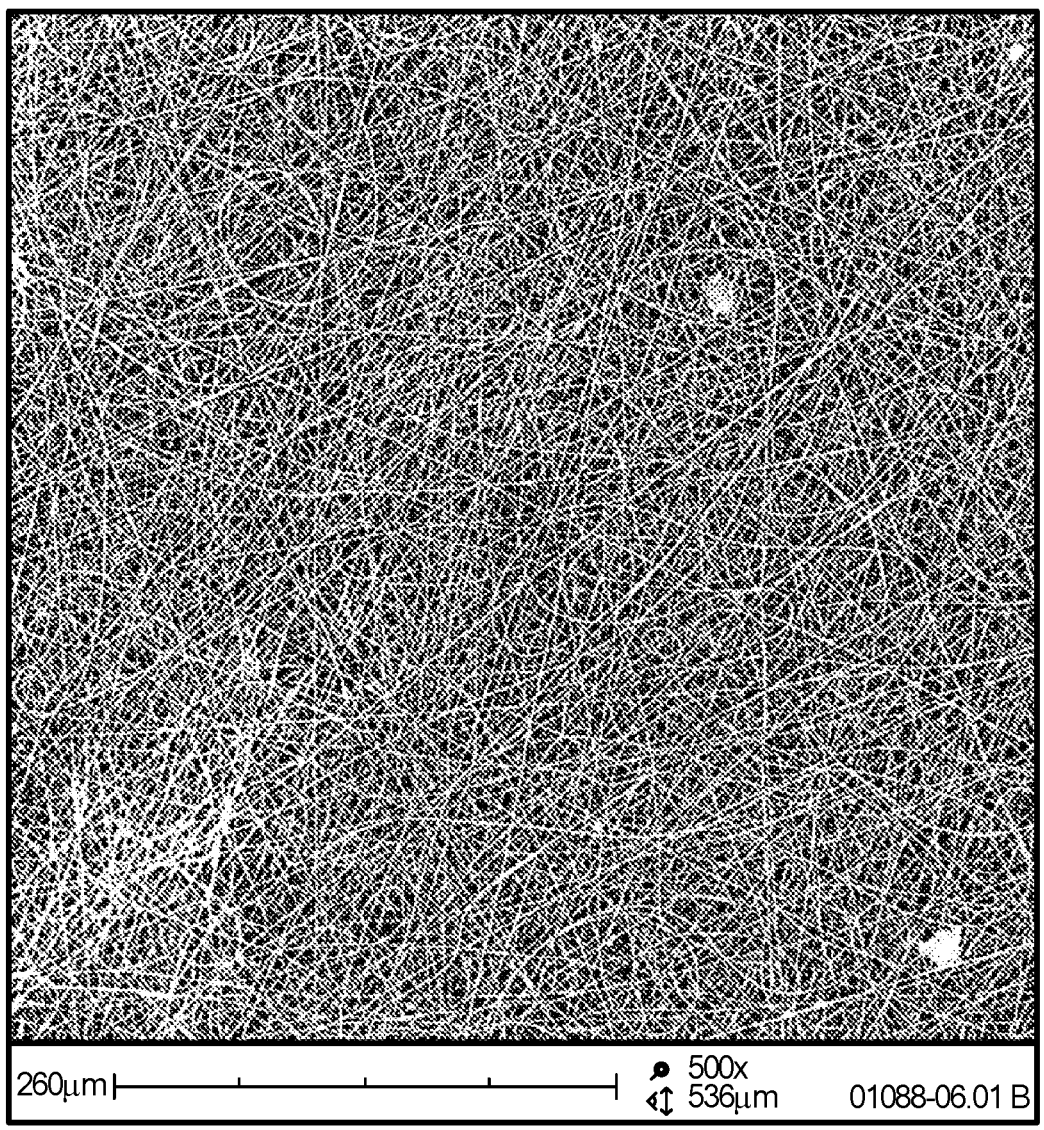
FIG. 2 is a SEM image and shows the bottom layer of the therapeutic composition as formed in Example 1.
Figure 3:
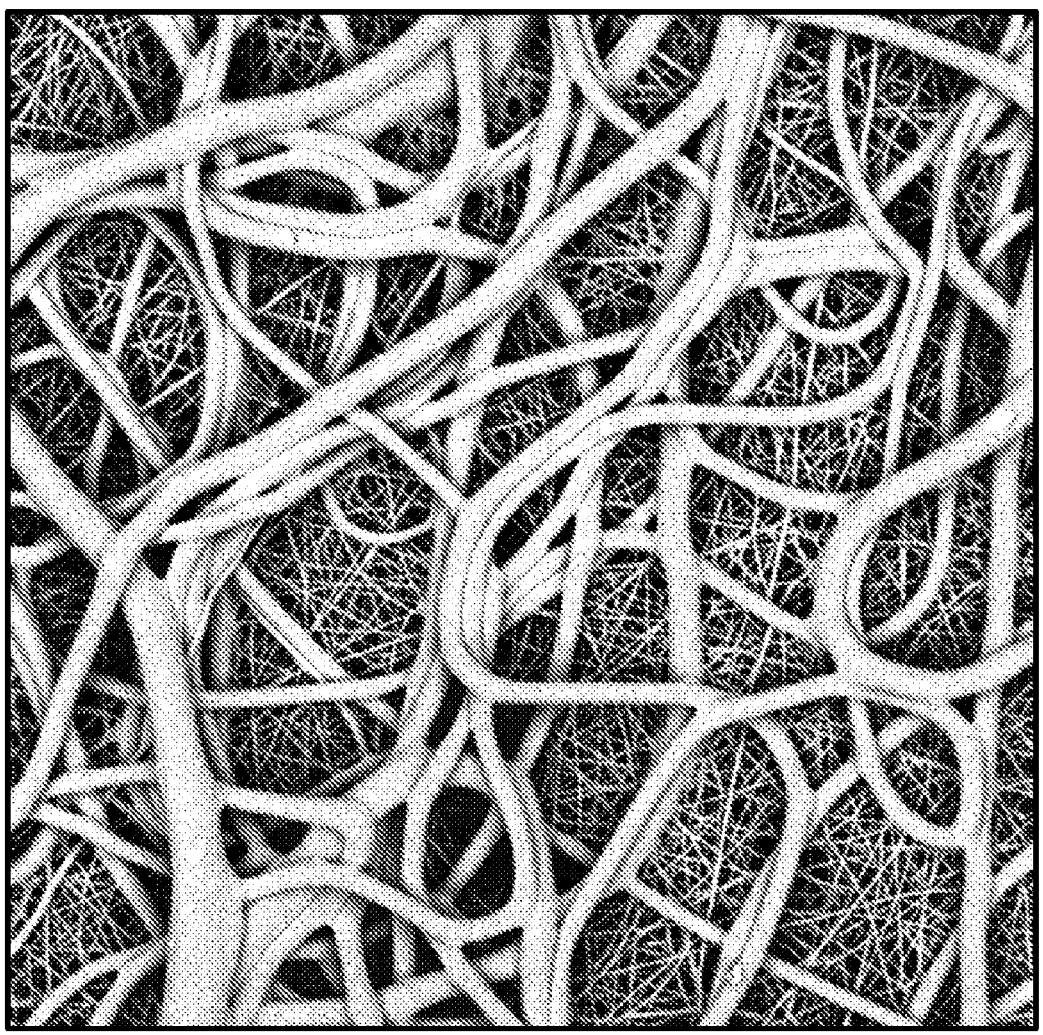
FIG. 3 is a SEM image and corresponds to a combination of the images in FIGS. 1 and 2 where both layers are visible.
Figure 4:
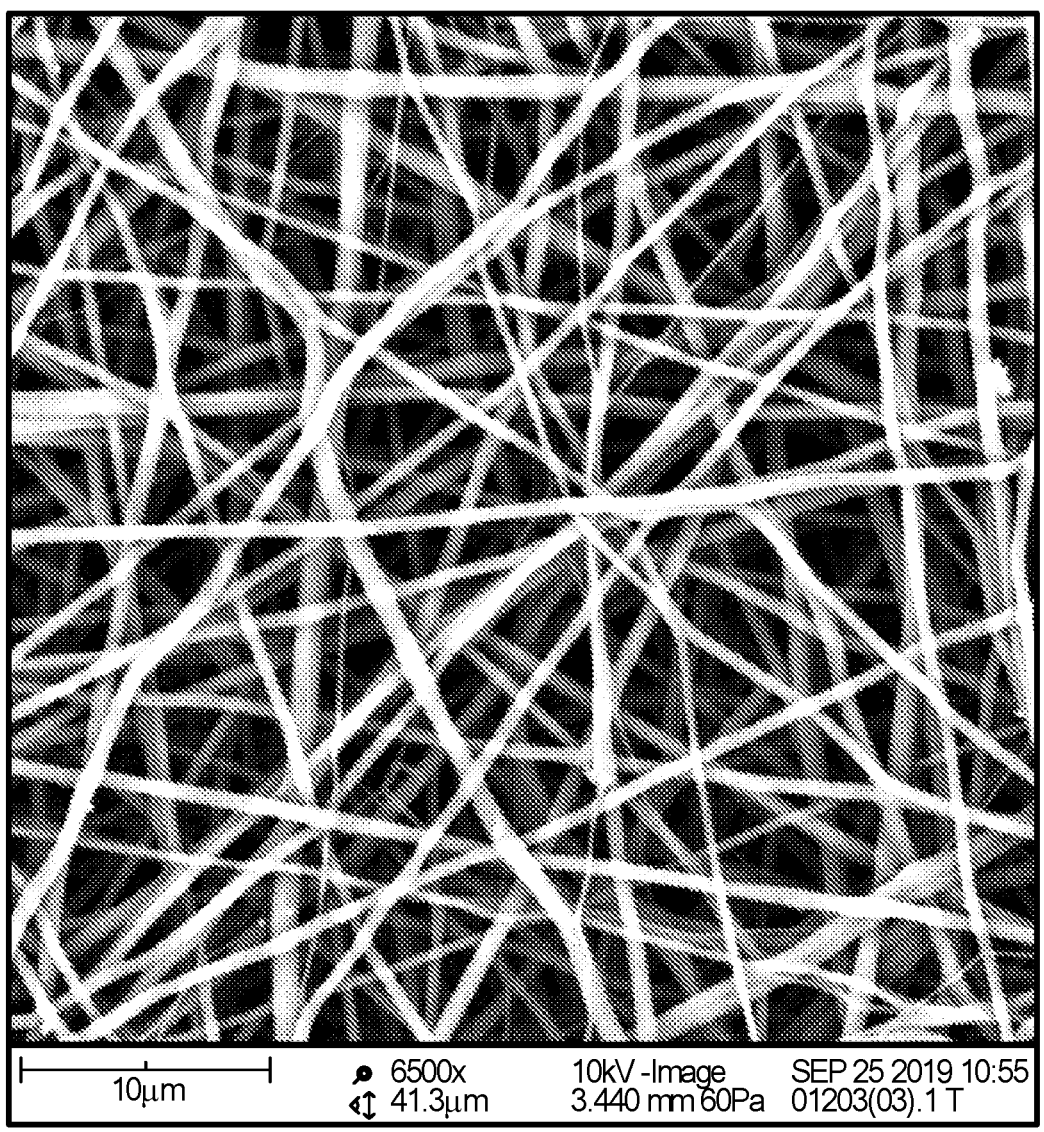
FIG. 4 is a scanning electron micrograph of the electrospun precursor made in Example 2.

The figures illustrate the layers. The file ending in T (FIG. 1) is the top layer and in B (FIG. 2) the bottom. The last image (FIG. 3) is a combination where both layers are visible.

Example 2: Electrospinning

A thermoplastic aromatic polycarbonate-based polyurethanes (PU) (Chronoflex, Advansource, US) was used in the manufacture of the device precursor/membranes by electrospinning. A solution containing 4 wt. % of PU in Hexafluoro-2-propanol (HFIP) (Sigma Aldrich, UK) was prepared. The electrospun precursor was prepared by delivering the polymer solution at a constant feed rate of 15 mL/h via a syringe pump and was electrospun vertically with an accelerating voltage of +20 kV DC-+8 kV. Temperature and relative humidity were kept constant (respectively at 25° C. and 40% RH) in a climate controlled electrospinning machine (LE-100, Bionicia, Spain). Fibers were collected on release paper sheets wrapped around a rotating collector positioned 25 cm from the tip of the needle. The collector was rotated at 100 RPM. Longitudinal translation was also applied, using a programmable motorized stage with a translation speed of 40 mm/s. Electrospinning was performed for 250 minutes to fabricate the desired sheet thickness, i.e. the desired thickness for the device precursor.

Fiber diameter, pore size and scaffold morphology characterization were performed by scanning electronic microscopy (SEM) (Phenom G2 Pro equipped with FiberMetric software, Phenom World, the Netherlands), using automated image characterization of multiple images in order to determine the mean fiber diameter and average pore size diameter. The FiberMetric software automatically identifies the location of the fibers within the captured SEM image and measures the diameter of each fiber 20 times at a specific location. Typically, around 100 of such measurements are performed per image. The diameter of the fibers can alternatively be obtained via manual measurements/analysis of multiple SEM images. The FiberMetric software also automatically measures the area of free space between fibers as a measure of pore size. The resulting data has been converted to average pore diameter, assuming circular pores as is standard practice, using Equation 1.

Equation 1—Formula used to convert average pore area (A) into average pore diameter (d).

Figure 1:
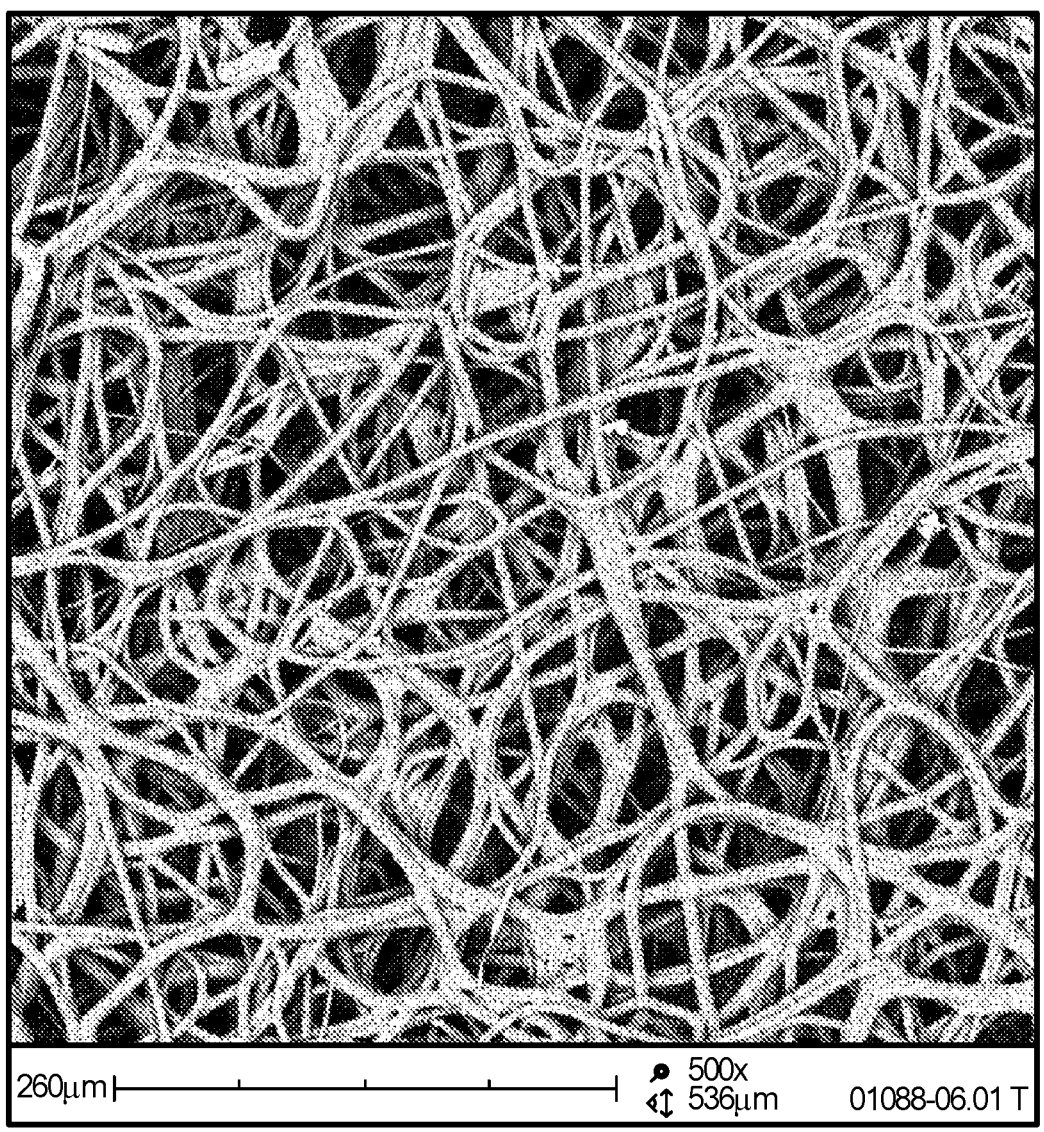
FIG. 1 is a SEM image and shows the top layer of a therapeutic composition as formed in Example 1.

The average fiber diameter of the fibers was 445 nm with a tolerance of 190 nm. The average pore diameter is 1.5 µm±0.8 µm. Thickness of the sheet is measured using a micrometer. The target average thickness of the material was 160 µm with a tolerance of 20%. FIG. 1 shows a scanning electron micrograph of the fibers produced using the above-mentioned method.

The fibrous mat was dried in a vacuum oven at ~10 mBar for over 24 hours at 25° C. to reduce the amount of residual solvent remaining from the fabrication process.

Post Process

Figure 5A:
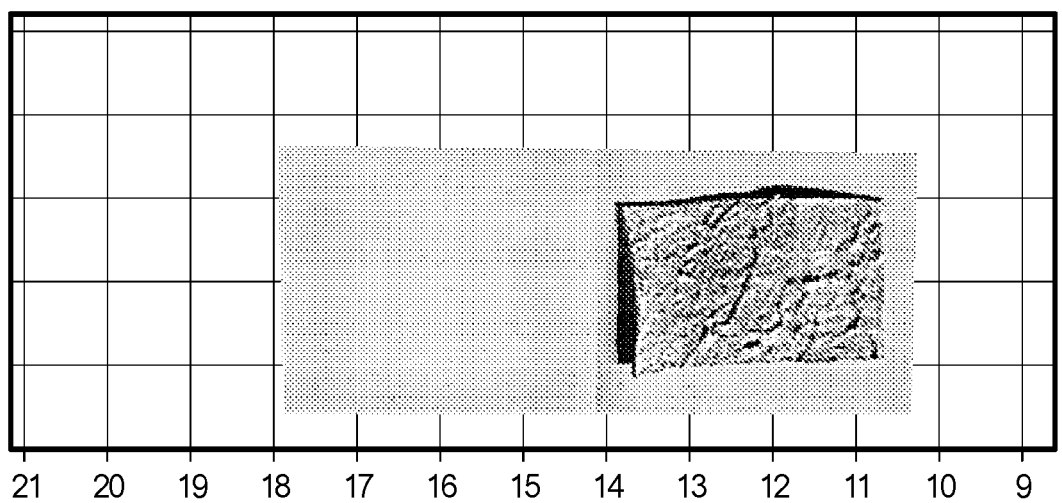
FIG. 5A shows an overview of how an electrospun precursor is folded prior to welding with a decellularized collagen membrane.
Figure 5B:
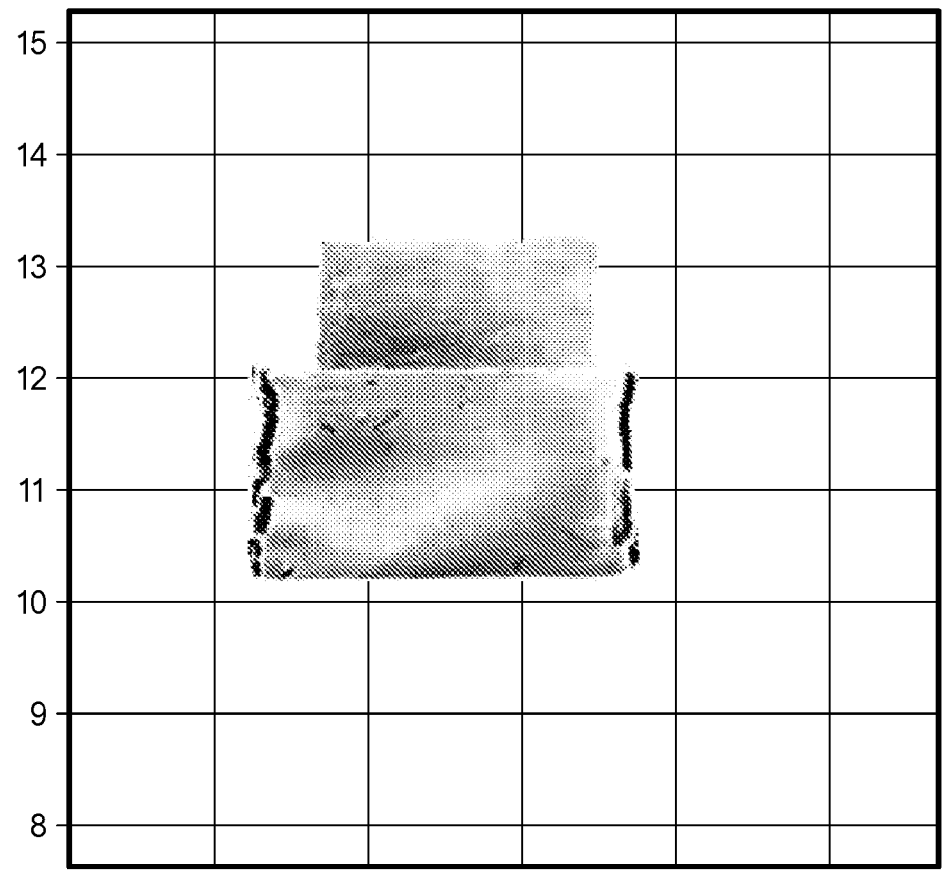
FIG. 5B shows a therapeutic composition with a ~60% surrounded decellularized collagen membrane.
Figure 5C:
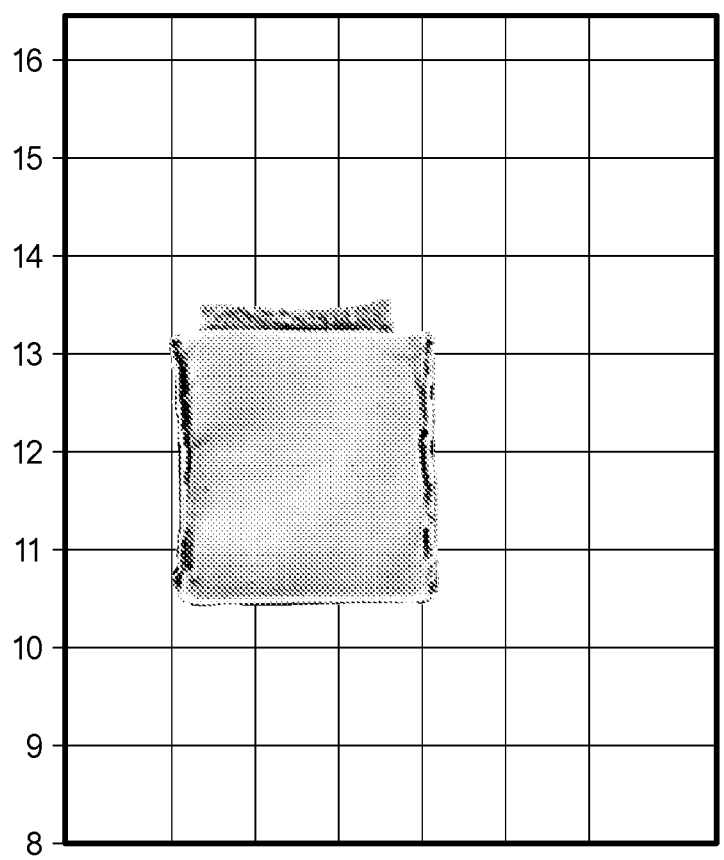
FIG. 5C shows a therapeutic composition with a ~80% surrounded decellularized collagen membrane.
Figure 5D:
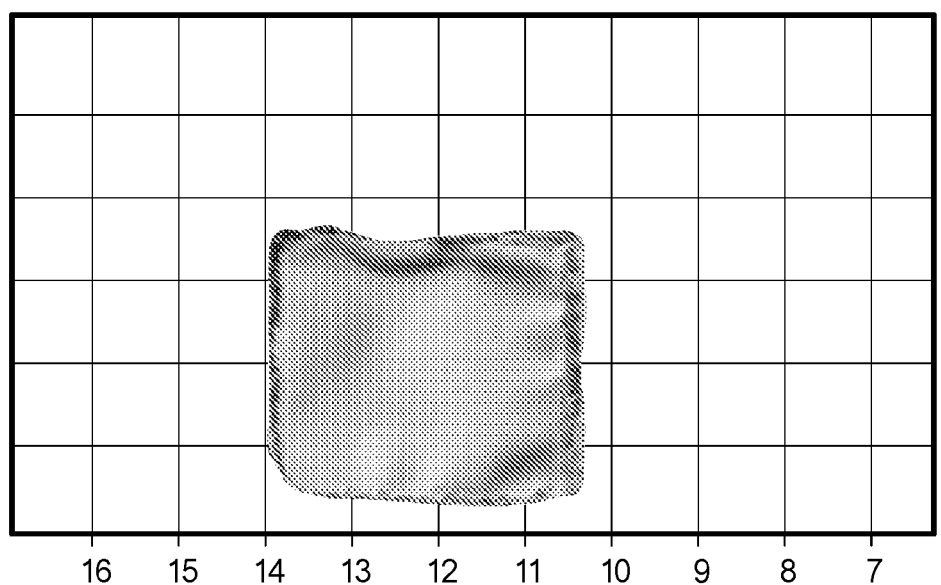
FIG. 5D shows a therapeutic composition with a 100% surrounded decellularized collagen membrane.

SURROUNDING A SOLID COMPOSITION: The scaffolds were fashioned into various proof of concept therapeutic compositions using a sonic welder. The electrospun precursor was cut into specific sizes and folded over and then sonically welded to itself (FIGS. 5A-C). A commercial decellularized collagen membrane (Chondro-Gide®, Geistlich) was enveloped/surrounded to different degrees, namely, ~60%, ~80% and 100%.

Figure 6A:
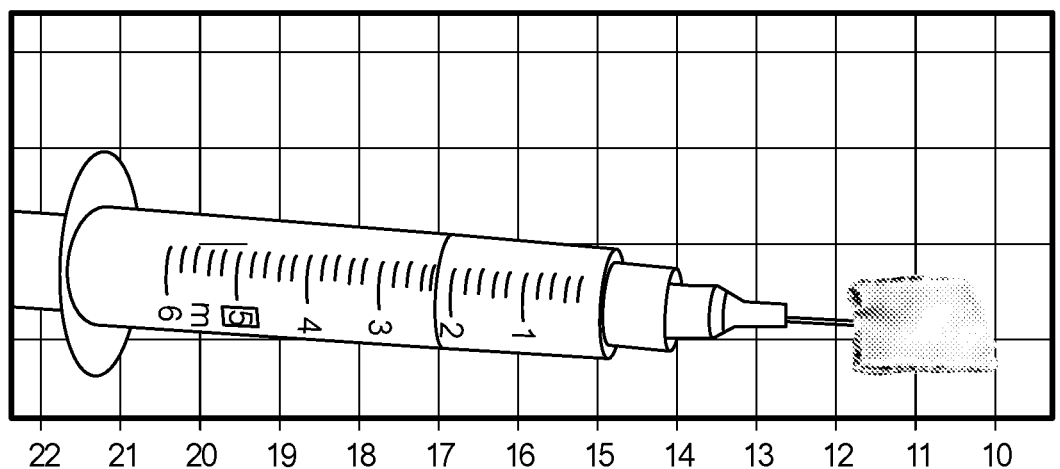
FIG. 6A shows a therapeutic composition made from an electrospun precursor with an entry port left open. The syringe contains a hydrogel that is injected into the "pouch."
Figure 6B:
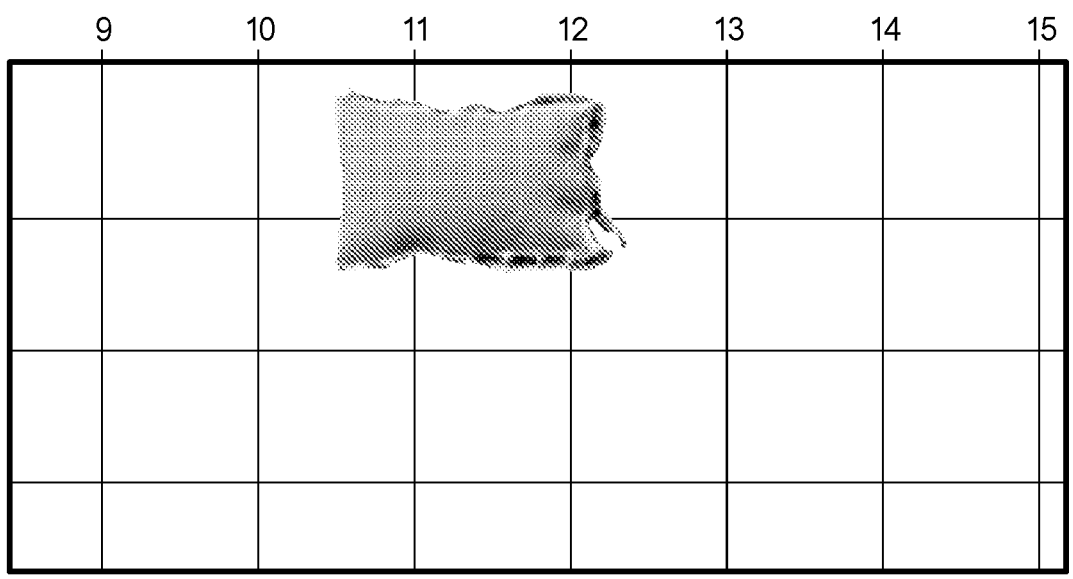
FIG. 6B shows a hydrogel filled therapeutic composition, where the electrospun membrane is wholly surrounding the hydrogel (i.e. 100% coverage).

SURROUNDING A LIQUID COMPOSITION: A hydrogel was prepared by dispersing 1 wt. % of hyaluronic acid in a 50/50 mix of distilled water and isopropanol. The mixture was left to homogenize for 24 hours on a roller mixer. An empty "pouch" was created using a sonic welder as mentioned above where a small entry port was left open. The hydrogel was filled into a syringe and injected into the "pouch" after which the sonic welder was utilized once again to close the entry port and create a fully surrounded therapeutic composition. See FIGS. 6A and 6B.

Cell Work

A study was carried out to show the release of a secreted protein from cells contained within a "pouch," manufactured from electrospun precursor material, following stimulation of the cells with an agent designed to induce the secretion of the protein when added to the external environment.

Experimental Design Overview

THP-1 cells are an immune derived cell line that, when stimulated with an appropriate agent, Lipopolysaccharide (LPS), secrete the interleukin IL-8. Levels of IL-8 secreted are proportional to concentrations of LPS administered to the cells. IL-8 can be detected using an ELISA-based immunoassay. Therefore the detection of IL-8 in the media surrounding the pouches demonstrates that the electrospun material allows a secreted protein such as IL-8 to move through the membrane. To examine the "escape" of cells from the "pouches," we measured levels of ATP in the media at the end of the experiment. ATP is manufactured by cells in a "just in time" manner and is not secreted, therefore detection of ATP in the external media would suggest contamination of the external environment with cells.

Methods

Electrospun material was folded and welded along edges as described above to form a bag with an opening along one short side. Each of the bags were designed to stand upright within a 24-well plate. Bags were placed into a 24-well plate using tweezers, one bag per well, such that the bag was supported by the walls of the well plate with the opening pointing upwards to allow media containing cells to be dispensed into the bag.

THP-1 cells, a nonadherent cell type, were used for the study. A stock of THP-1 cells was cultured in a T175 cm$^2$ flask. An aliquot of these cells was counted using a Luna cell counting instrument and diluted to a concentration of 200,000 cells per mL, then 500 μL of this stock was dispensed into the opening in the bag (100,000 cells per t-bag per well). In addition, 1 mL of identical media (without cells) was dispensed rapidly into the well but external to the bag. The 24-well plate containing the bags was then incubated at 37° C., 5% C02 and 95% humidity for 24 hours.

After 24 hours, various concentrations of Lipo Poly Saccharide (LPS, bacterial cell wall extract) were added to the media external to the bag by removing 500 μL of media from each well and readministering 500 μL of media containing LPS at 2× concentration. The plate was then reincubated for 24, 48, 72 and 96 hours and at each time point a small aliquot of media (70 μL) was removed from the external solution and frozen (−30° C.) for later assay.

Detection of IL-8 in Media

Figure 7:
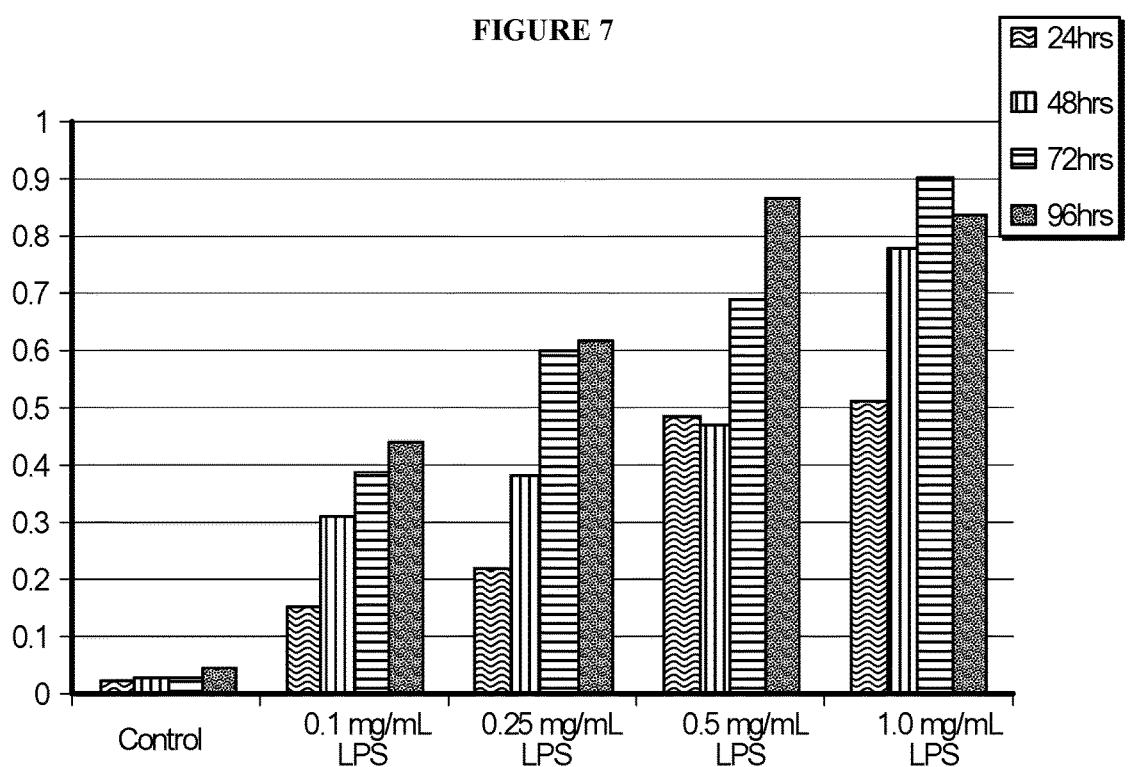
FIG. 7 shows Il-8 release as measured by ELISA as a response of LPS concentration.

A plate-based ELISA system was used to detect the level of IL-8 released from the cells into the media. Briefly, immunoabsorbant plates were coated with a primary antibody to human IL-8 according to the manufacturer's instructions. Aliquots (20 μL) of media that had been removed from the external environment at defined time points were added to the immunoassay plate and allowed to interact with the antibody coated plate overnight at 4° C. Wells were then washed with buffer to remove the media and unbound material and a secondary antibody labelled with horse radish peroxidase (HRP) was added to all wells, washed to remove unbound secondary antibody then treated with HRP substrate. The HRP signal is therefore proportional to the amount of IL-8 in the media. FIG. 7 shows the measured IL-8 signal of various experimental conditions. The data shows that there is a dose response of the THP-1 cells with the amount of LPS added and that the "pouches" allow both IL-8 and LPS to pass through the membrane. The interior of the pouch provided a good environment for the cells and the cells stayed alive for the duration of the experiment.

Detection of ATP

Figure 8:
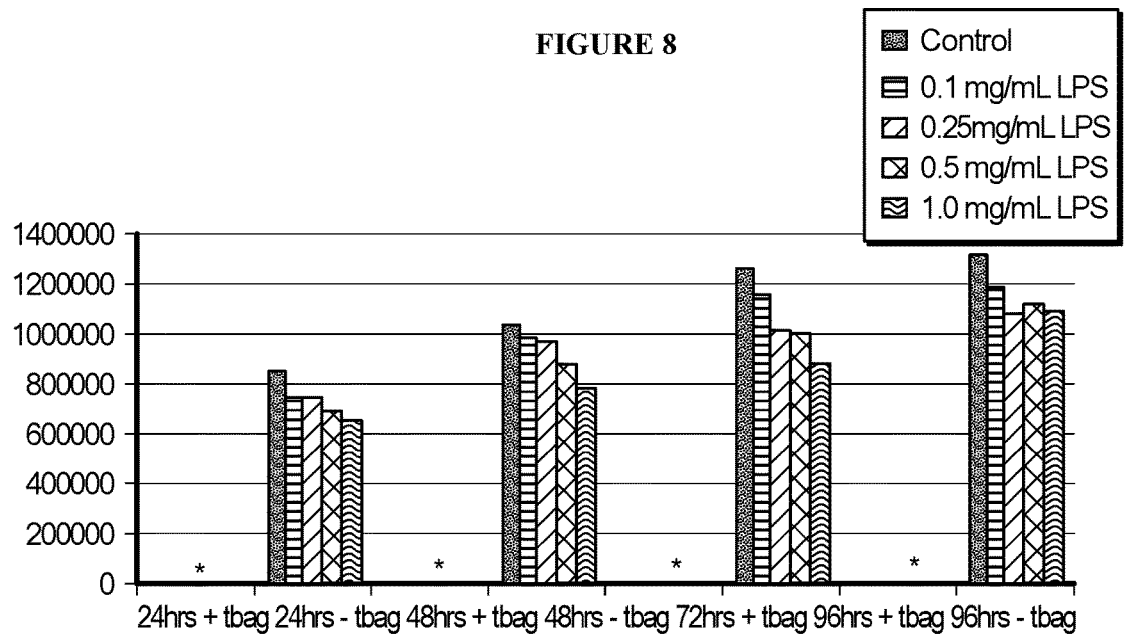
FIG. 8 shows ATP detection in the media. Samples labelled with an asterisk (*) are from wells with the bags removed. The signal detected does not appear on the graphs as they are too low. The other series represents ATP release from control wells with THP-1 cells in the wells.

To detect cells released from the bag into the external environment, at the end of the experiment bags were physically removed from the well plate using tweezers and placed into a separate plate. Media from each well was mixed with a 1 mL pipette and transferred into a 1.5 mL centrifuge tube, one tube per well. Tubes were centrifuges at 800 g for 5 mins to pellet any cells in the tube. The media was removed by aspiration being careful to leave a small volume (approx. 50 μL) in the tube. The Promega ATP GLO detection reagents were then used (per the manufacturer protocol) to detect the concentration of ATP in each tube. ATP will only be present if cells are present in the tube and therefore this readout is proportional to the number of cells in the tube. FIG. 8 shows the detection of ATP in wells with the bags removed (marked with an asterisk [*]) and the detection of ATP in well with cells present. The data clearly shows that no cells were able to escape the pouched for the duration of the experiments.

Visual Inspection of the Wells Post Assay

In addition to detecting ATP, the 24-well microplate was visually inspected using the microscope after the removal of the media to identify any cells either adhered to the well or remaining in the plate after aspiration of the media. No cells were detected.

Figure 9:
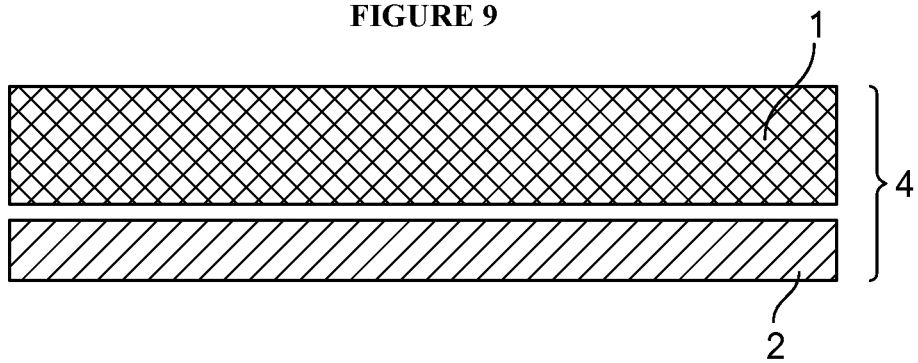
FIG. 9 shows a flat, bilayered biocompatible membrane (4) comprising a layer (1) with smaller diameter fibers and a second layer (2) with larger diameter fibers. The layers are not shown to scale and one may or may not be thicker than the other.
Figure 11:
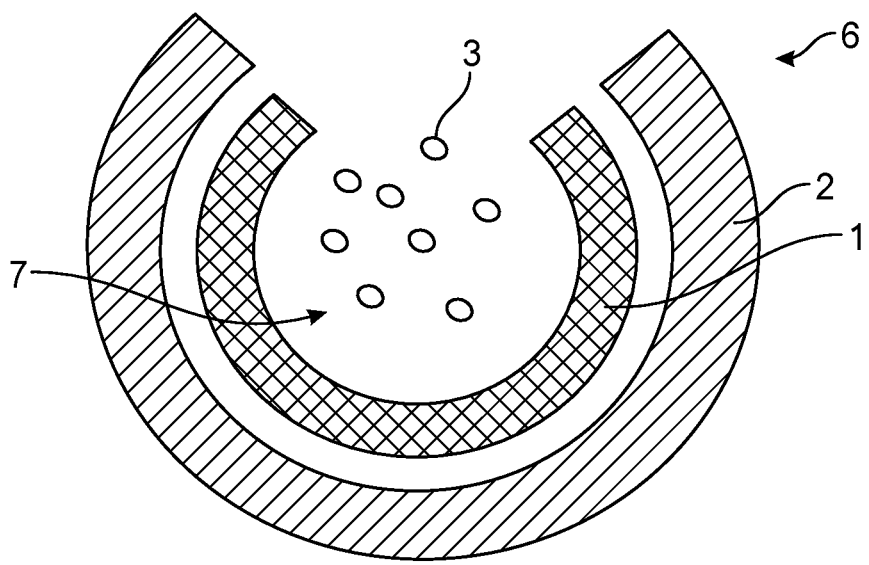
FIG. 11 shows biocompatible membrane (4) from FIG. 9 being folded (in 2D, but equally this applies in 3D) the bag or pouch (6) in FIG. 11, such the layer (1) with the smaller diameter fibers faces internally, so as to be contactable with the therapeutic agent (in this case cells [3] supported on a carrier [8]) that may be placed within the inner portion (7) of the bag or pouch (6). Layer (1) may here also replace the need for a carrier or may interface with a further carrier such as a hydrogel. The layer (2) with the larger diameter fibers faces externally, so as to be contactable with the subcutaneous environment of the patient into which the bag or pouch (6) is to be provided.

Example 3: Preparation of a Bag or Pouch with Larger Diameter Fibers on External Surface A flat sheet of the biocompatible membrane (4) shown in FIG. 9 is folded into the bag or pouch (5) in FIG. 11, such the layer (2) with the larger diameter fibers faces externally, so as to be contactable with the subcutaneous environment of the patient into which the bag or pouch (5) is to be provided. The layer (1) with the smaller diameter fibers faces internally, so as to be contactable with the therapeutic agent (in this case cells [3]) that may be placed within the bag or pouch (5).

Example 4: Preparation of a Bag or Pouch with Larger Diameter Fibers on Internal Surface As for Example 3, above, but the flat sheet of the biocompatible membrane (4) shown in FIG. 9 is folded into the bag or pouch (6) in FIG. 10, such the layer (2) with the larger diameter fibers faces internally, so as to be contactable with the therapeutic agent (in this case cells [3]) that may be placed within the bag or pouch (6). The layer (1) with the smaller diameter fibers faces externally, so as to be contactable with the subcutaneous environment of the patient into which the bag or pouch (6) is to be provided.

Example 5: Preparation of a Bag or Pouch in the Shape of a Biconcave Disc

Figure 12:
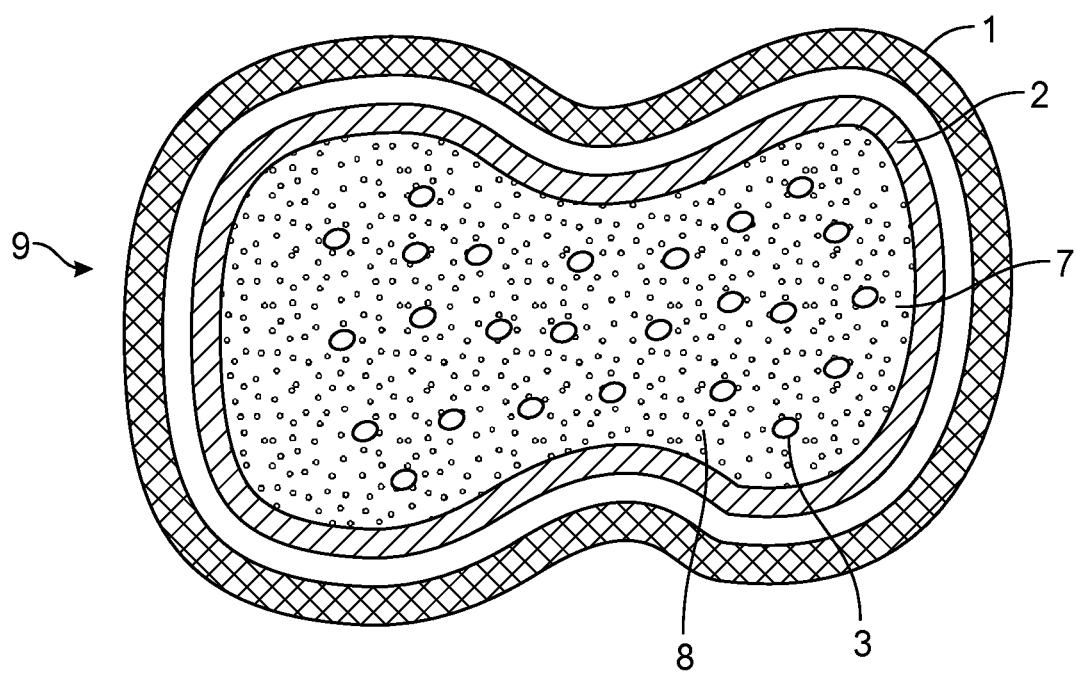
FIG. 12 shows biocompatible membrane (4) from FIG. 9 being folded (in 2D, but equally this applies in 3D) to form one arrangement whereby the layer (1) with the smaller diameter fibers faces externally, so as to be contactable with the subcutaneous environment of the patient into which the bag or pouch (5) is to be provided. In this embodiment the biocompatible membrane is folded and prepared in such a way to render the resulting bag or pouch (9) a biconcave disc, which contains the inner portion (7), itself containing the therapeutic agent (in this case cells [3] supported on a carrier [8]).

Taking either Example 2 or 3 as a starting point, the design of the pouch or bag can be enhanced such that is resembles a biconcave disc (9), as shown in FIG. 12. In FIG. 12, the biocompatible membrane (4) has been folded (in 2D, but equally this applies in 3D) to form one arrangement whereby the layer (1) with the smaller diameter fibers faces externally, so as to be contactable with the subcutaneous environment of the patient into which the bag or pouch (5) is to be provided. In this embodiment the biocompatible membrane is folded and prepared in such a way to render the resulting bag or pouch (9) a biconcave disc, which contains the inner portion (7), itself containing the therapeutic agent (in this case cells [3] supported on a carrier [8]). FIG. 12 shows an example where the outermost layer contains the fibers with smaller diameter; the opposite situation, where the layers are swapped and the fibers with larger diameter are at the external surface, adopts the correspondingly similar structure. An O-ring of suitable material may, for example, be used to help form and maintain the biconcave disc shape by providing structure around the periphery of the biconcave disc.

Example 6: Preparation of a Tri-Layer Membrane and Associated Bag or Pouch

Figure 13A:
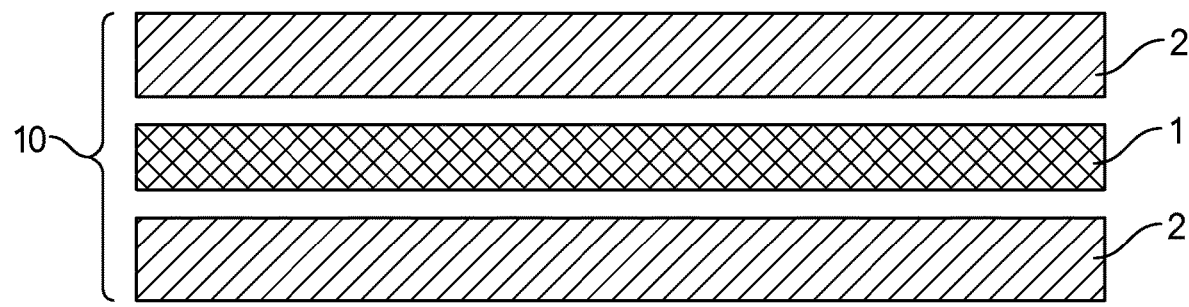
FIG. 13A shows a trilayered biocompatible membrane (10) comprising a first layer (1) with smaller diameter fibers between second two layers (2) with larger diameter fibers.
Figure 13B:
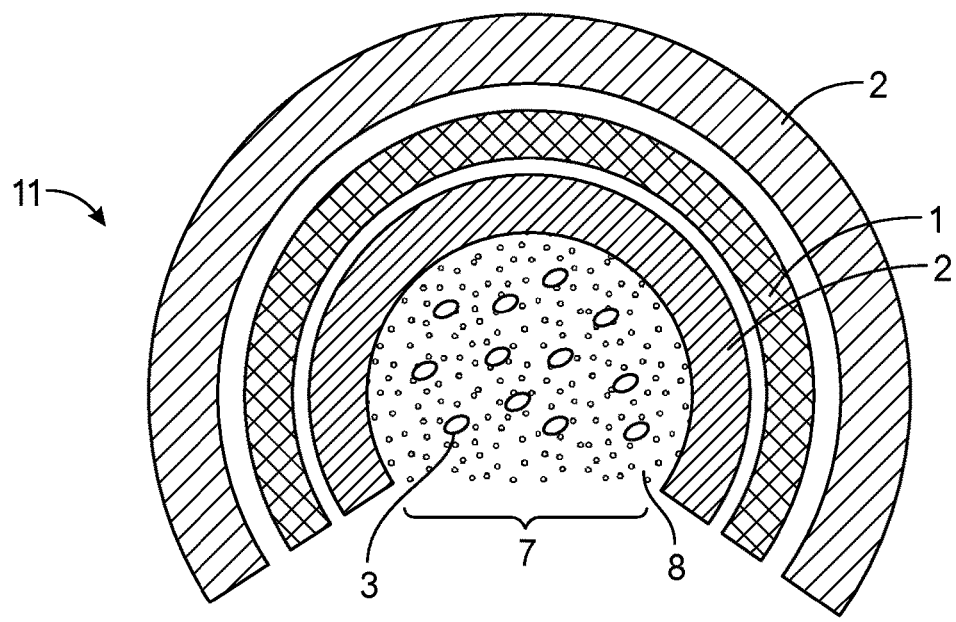
FIG. 13B shows trilayered biocompatible membrane (10) from FIG. 13A being folded (in 2D, but equally this applies in 3D) to form a bag or pouch (11) wherein the external layer (2) with the larger diameter fibers is contactable with the subcutaneous environment of the patient in which the bag or pouch is to be provided and the internal layer (2) with the larger diameter fibers is contactable with the inner portion (7) which contains the therapeutic agent (in this case cells [3] supported on a carrier [8]). The layer (1) with the smaller diameter fibers is located between the two layers (2) with the larger diameter fibers, and directly contacts neither the external subcutaneous environment of the patient nor the inner portion (7) of the bag or pouch.

A trilayered biocompatible membrane (10), as shown in FIG. 13A, comprising a layer (1) with smaller diameter fibers between two layers (2) with larger diameter fibers can be formed by electrospinning. This trilayered membrane (10) can be used to form a bag or pouch in the same manner to the bilayered membranes discussed above, resulting in a trilayered bag or pouch as shown in FIG. 13B, being formed from the folding of trilayered membrane (10) (in 2D, but equally this applies in 3D) to form a bag or pouch (11) wherein the external layer (2) with the larger diameter fibers is contactable with the subcutaneous environment of the patient in which the bag or pouch is to be provided and the internal layer (2) with the larger diameter fibers is contactable with the inner portion (7) which contains the therapeutic agent (in this case cells [3] supported on a carrier [8]). The layer (1) with the smaller diameter fibers is located between the two layers (2) with the larger diameter fibers, and ideally directly contacts neither the external subcutaneous environment of the patient nor the inner portion (7) of the bag or pouch.

What is claimed is:

1. A therapeutic composition (5,6) comprising an inner portion (7) and a biocompatible membrane (4, 10) fully or partially surrounding the inner portion; wherein the biocompatible membrane comprises at least two layers:
   a first layer (1) of a porous, non-woven network of thermoplastic polyurethane polymer fibres formed by electrospinning and having a porosity of greater than or equal to 50%; an average pore diameter of less than 5 µm; and has a thickness in the range of 10 to 250 µm; wherein the first layer is non-biodegradable; and
   a second layer (2) of a porous, non-woven network of thermoplastic polymer fibres formed by electrospinning, the second layer (2) having a porosity which is substantially equal to or higher than the porosity of the first layer (1); and/or wherein the mean average fibre diameter of the second layer (2) is greater than the mean average fibre diameter in the first layer (1); and/or wherein the average pore diameter of the second layer (2) is greater than the average pore diameter of the first layer (1); and
   wherein the inner portion (7) comprises a therapeutic agent (3).

2. The therapeutic composition according to claim 1, wherein the biocompatible membrane (4, 10) is in the form a pouch or bag (5, 6, 11) which partially or fully encapsulates the inner portion (7) comprising the therapeutic agent (3).

3. The therapeutic composition according to claim 2, further comprising a carrier (8) on or in which the therapeutic agent (3) is disposed.

4. The therapeutic composition according to claim 2, wherein the pouch or bag (6) is arranged such that the first layer (1) faces or is in contact with the encapsulated inner portion (7); whilst the second layer (2) faces externally.

5. The therapeutic composition according to claim 2, wherein the pouch or bag (5) is arranged such that the first layer (1) faces externally; whilst the second layer (2) faces or is in contact with the encapsulated inner portion (7).

6. The therapeutic composition according to claim 3, wherein the pouch or bag (5) is arranged such that the first layer (1) faces externally; whilst the second layer (2) faces or is in contact with the encapsulated inner portion (7), the carrier (8).

7. The therapeutic composition according to claim 2, wherein the biocompatible membrane (10) comprises three layers: the first layer (1) provided between two second layers (2), wherein the inner portion (7) is provided within an internal-facing surface of one of the second layers (2) when the biocompatible membrane (4) is in the form the pouch or bag (11); with the other of the two second layers (2) providing an external-facing surface.

8. The therapeutic composition according to claim 1, wherein the first layer (1) has a porosity in the range of 50% to 90%.

9. The therapeutic composition according to claim 1, wherein the first layer (1) has an average pore diameter of less than 2 µm.

10. The therapeutic composition according to claim 1, wherein the first layer (1) has a thickness in the range of 10 to 150 µm.

11. The therapeutic composition according to claim 1, wherein the mean diameter of the polymer fibres of the first layer (1) is less than 700 nm.

12. The therapeutic composition according to claim 1, wherein the second layer (2) is or comprises polyurethane or any other biocompatible, thermoplastic polymer or polymer blend.

13. The therapeutic composition according to claim 1, wherein the first layer (1) and the second layer (2) of the biocompatible membrane (4, 10) are non-biodegradable.

14. The therapeutic composition according to claim 1, wherein the therapeutic agent (3) is selected from therapeutic cells, a drug, a nucleic acid, a polynucleotide, a protein, a polypeptide, an antibody, a lipid nanoparticle, an extracellular vesicle, and an exosome.

15. The therapeutic composition according to claim 3, wherein the biocompatible membrane (4) fully or partially surrounds the carrier.

16. The therapeutic composition according to claim 3, wherein the carrier (8) comprises a porous, non-woven network of polymer fibres or a hydrogel, gelatin, collagen or decellularized tissue.

17. The therapeutic composition according to claim 1, comprising cells (3).

18. The therapeutic composition according to claim 4, wherein the externally-facing second layer further comprises a hydrogel, gelatin or collagen, or decellularized tissue.

19. The therapeutic composition according to claim 1, wherein the second layer (2) is formed from electrospun fibres, and
   (i) the porosity is in the range of 70 to 98%; and/or
   (ii) the average pore diameter is in the range of 5 to 80 µm; and/or
   (iii) the mean diameter of the polymer fibres is in the range of 1 to 10 µm.

20. The therapeutic composition according to claim 1, wherein
   (i) the porosity of the second layer (2) is within at least 120%, 110%, 100% of the porosity of the first layer (1); and/or
   (ii) the average pore size/diameter of the second layer (2) is at least 2 times, at least 5 times, at least 10 times, at least 20 times, at least 50 times or at least 100 times the pore size/diameter of the first layer (1); and/or
   (iii) the mean diameter of the polymer fibres of the second layer (2) is at least 2 times, at least 5 times, at least 10 times, at least 20 times, at least 50 times or at least 100 times the diameter of the first layer (1).

21. The therapeutic composition according to claim 1, which further comprises one or more additives wherein the additives are selected from growth factors, enzymes, oxygen-releasing materials, and bone growth promoting materials.

22. A membrane comprising at least two layers, wherein
   (i) the first layer (1) is a biocompatible, non-biodegradable membrane comprising a porous, non-woven network of thermoplastic polyurethane polymer fibres formed by electrospinning, wherein the biocompatible membrane has a porosity of greater than or equal to 50%; an average pore diameter of less than 5 µm; and has a thickness in the range of 10 to 250 µm; and (ii) the second layer (2) is disposed on the first layer and wherein the second layer (2) is of a porous, non-woven network of thermoplastic polymer fibres formed by electrospinning;

which fibres of the second layer (2) may or may not be polyurethane, the second layer (2) having a porosity which is substantially equal to or higher than the porosity of the first layer (1); and/or wherein the second layer (2) having a mean average fibre diameter of the second layer (2) greater than the mean average fibre diameter in the first layer (1);

and/or wherein the average pore diameter of the second layer (2) is greater than the average pore diameter of the first layer (1).

23. A device comprising a therapeutic composition and cells, said therapeutic comprising an inner portion (7) and a biocompatible membrane (4, 10) fully or partially surrounding the inner portion; wherein the biocompatible membrane comprises at least two layers:

a first layer (1) of a porous, nonwoven network of thermoplastic polyurethane polymer fibres formed by electrospinning and having a porosity of greater than or equal to 50%; an average pore diameter of less than 5 µm; and has a thickness in the range of 10 to 250 µm; wherein the first layer is nonbiodegradable; and a second layer (2) of a porous, non-woven network of thermoplastic polymer fibres formed by electrospinning, the second layer (2) having a porosity which is substantially equal to or higher than the porosity of first layer (1); and/or wherein the mean average fibre diameter of the second layer (2) is greater than the mean average fibre diameter in the first layer (1); and/or wherein the average pore diameter of the second layer (2) is greater than the average pore diameter of the first layer (1); and wherein the inner portion (7) comprises a therapeutic agent (3), wherein the inner portion (7) comprises the cells selected from the group consisting of:

pancreatic beta or islet cells, with or without a carrier material (8);

hepatocytes, erythrocytes, leukocytes and combinations thereof.

* * * * *